US011647909B2

(12) United States Patent
Van Der Poel et al.

(10) Patent No.: US 11,647,909 B2
(45) Date of Patent: *May 16, 2023

(54) 3D INTRAORAL SCANNER MEASURING FLUORESCENCE

(71) Applicant: 3Shape A/S, Copenhagen (DK)

(72) Inventors: Mike Van Der Poel, Rødovre (DK); Karl-Josef Hollenbeck, Copenhagen (DK)

(73) Assignee: 3SHAPE A/S, Copenhagen (DK)

(*) Notice: Subject to any disclaimer, the term of this patent is extended or adjusted under 35 U.S.C. 154(b) by 70 days.

This patent is subject to a terminal disclaimer.

(21) Appl. No.: 16/512,583

(22) Filed: Jul. 16, 2019

(65) Prior Publication Data

US 2019/0365236 A1 Dec. 5, 2019

Related U.S. Application Data

(63) Continuation of application No. 16/283,020, filed on Feb. 22, 2019, now Pat. No. 10,905,333, which is a (Continued)

(30) Foreign Application Priority Data

Jun. 29, 2012 (DK) .............. PA 2012 70382

(51) Int. Cl.
*A61B 5/00* (2006.01)
*A61C 9/00* (2006.01)

(52) U.S. Cl.
CPC .......... *A61B 5/0088* (2013.01); *A61B 5/0071* (2013.01); *A61B 5/742* (2013.01); *A61C 9/0053* (2013.01); *A61B 5/0035* (2013.01)

(58) Field of Classification Search
CPC ..... A61C 9/0053; A61B 5/0088; A61B 5/742; A61B 5/035
(Continued)

(56) References Cited

U.S. PATENT DOCUMENTS 6,263,234 B1 7/2001 Engelhardt et al.
6,522,407 B2 2/2003 Everett et al.
(Continued)

FOREIGN PATENT DOCUMENTS

EP 2 039 288 A1 3/2009
JP 2004 313470 A 11/2004
(Continued)

OTHER PUBLICATIONS

Extended European Search Report dated Dec. 17, 2015, issued by the European Patent Office in corresponding European Application No. 13809950.2-1657, (8 pages).
(Continued)

*Primary Examiner* — Nicholas D Lucchesi
(74) *Attorney, Agent, or Firm* — Buchanan Ingersoll & Rooney P.C.

(57) ABSTRACT

A 3D scanner system for detecting and/or visualizing cariogenic regions in teeth based on fluorescence emitted from said teeth, the 3D scanner system including data processing means configured for mapping a representation of fluorescence emitted from the teeth onto the corresponding portion of a digital 3D representation of the teeth to provide a combined digital 3D representation.

15 Claims, 5 Drawing Sheets

Related U.S. Application Data continuation of application No. 16/264,835, filed on Feb. 1, 2019, now Pat. No. 11,246,490, which is a continuation of application No. 14/411,160, filed as application No. PCT/DK2013/050213 on Jun. 27, 2013, now Pat. No. 10,238,296.

(60) Provisional application No. 61/665,015, filed on Jun. 27, 2012.

(58) Field of Classification Search
USPC .......................................................... 433/29
See application file for complete search history.

(56) References Cited

U.S. PATENT DOCUMENTS

| | | | |
|---|---|---|---|
| 7,698,068 | B2 | 4/2010 | Babayoff |
| 7,929,151 | B2 | 4/2011 | Liang et al. |
| 8,077,949 | B2 | 12/2011 | Liang et al. |
| 8,520,922 | B2 | 8/2013 | Wang et al. |
| 8,556,625 | B2 | 10/2013 | Lovely |
| 8,687,859 | B2 | 4/2014 | Yan et al. |
| 8,768,016 | B2 | 7/2014 | Pan et al. |
| 8,908,936 | B2 | 12/2014 | Yan et al. |
| 10,390,913 | B2 * | 8/2019 | Sabina ............... A61B 1/00186 |
| 10,905,333 | B2 * | 2/2021 | Van Der Poel ...... A61B 5/0088 |
| 2003/0130576 | A1 | 7/2003 | Seeley et al. |
| 2005/0090749 | A1 | 4/2005 | Rubbert |
| 2005/0182321 | A1 | 8/2005 | Frangioni |
| 2005/0203420 | A1 | 9/2005 | Kleen et al. |
| 2008/0062429 | A1 | 3/2008 | Liang et al. |
| 2008/0063998 | A1 | 3/2008 | Liang et al. |
| 2008/0094631 | A1 | 4/2008 | Jung et al. |
| 2009/0296045 | A1 | 12/2009 | Lo et al. |
| 2010/0216087 | A1 | 8/2010 | Hennig |
| 2010/0253773 | A1 | 10/2010 | Oota et al. |
| 2012/0013722 | A1 | 1/2012 | Wong et al. |
| 2012/0092461 | A1 | 4/2012 | Fisker et al. |
| 2012/0237890 | A1 | 9/2012 | Liang et al. |
| 2013/0189641 | A1 | 7/2013 | Perfect et al. |

FOREIGN PATENT DOCUMENTS

| | | | |
|---|---|---|---|
| JP | 2007 296249 | A | 11/2007 |
| JP | 2009 090091 | A | 4/2009 |
| WO | 2010/145669 | A1 | 12/2010 |
| WO | 2011/140664 | A2 | 11/2011 |
| WO | 2012/007769 | A1 | 1/2012 |

OTHER PUBLICATIONS

International Search Report (PCT/ISA/210) dated Sep. 18, 2013, by the Danish Patent Office as the International Searching Authority for International Application No. PCT/DK2013/050213.

B.T. Amaechi et al., "Use of Quantitative Light-induced Fluorescence to Monitor Tooth Whitening"Lasers in Dentistry VII, Proceedings of SPIE, vol. 4249, (2001), oo. 157-162.

B Angmar-Mansson et al. "Quantitative light-induced fluorescence (QLF): a method for assessment of incipient caries lesions", Dentomaxillofacial Radioloqv, (2001), vol. 30, DD, 298-307.

Callieri M, Clgnoni et al. "Reconstructing textured meshes from multiple range + rgb maps", VMV 2002, Erlangen, Nov. 20-22, 2002, pp. 665-666.

R.L. Hartles et al., "The Fluorescence of Teeth under Ultraviolet Irradiation", Biochemical Journal, vol. 54, No. 4, Jan. 13, 1953, oo. 632-638.

Thomas Kronfeld et al., "Snake-Based Segmentation ofTeeth from Virtual Dental Casts", Computer-Aided Desiqn & Applications, 7(2), 2010, DD. 221-233.

ML Sinyaeva et al., "Fluorescence Diagnostics in Dentistry", Laser Physics, vol. 14, No. 8, 2004, pp. 1132-1140.

An English Translation of the Office Action (Notice of Reasons for Rejection) dated Mar. 21, 2017, by the Japanese Patent Office in Japanese Patent Application No. 2015-518849. (6 pages).

Office Action (Notice of Reasons for Rejection) dated Nov. 21, 2017, by the Japanese Patent Office in Japanese Patent Application No. 2015-518849; and English Translation (11 pages in total).

Petition for Inter Partes Review of U.S. Pat. No. 10,905,333—IRP2021-01312, Case No. IPR2021-01312 U.S. Pat. No. 10,905,333, 77 pages.

Exhibit 1002—Declaration of Rongguang Liang, PH.D. U.S. Pat. No. 10,905,333, Align Technology, Inc. Petitioner, 124 pages.

Exhibit 1003—Liang CV, 13 pages.

Exhibit 1004—U.S. Pat. No. 10,905,333 File History, 334 pages.

Exhibit 1005—U.S. Appl. No. 16/264,835 File History, 369 pages.

Exhibit 1012—Imaging Diagnostics of Dental Diseases and Conditions (Caries, Periodontal Disease, Cracked Teeth, and Pulp Vitality) [SBIR R43/R44], 18 pages.

Exhibit 1013—Boye, U. et al."Comparison of photographic and visual assessment of occlusal caries with histology as the reference standard" BMC Oral Health, 2012, vol. 12, No. 10, 6 pages.

Exhibit 1014—Braga, M. M., et al."Detection Activity Assessment and Diagnosis of Dental Caries Lesions" 2010 Elsevier Inc., Jun. 23, 2021, 15 pages.

Exhibit 1015—Align Technology Inc.'s Opening Claim Construction Brief, 31 pages.

Exhibit 1016—3Shape Trios A/S and 3Shape A/S's Responsive Claim Construction Brief, 122 pages.

Exhibit 1017—In the United States District Court for the Western District of Texas Waco Division, 20 pages.

Exhibit 1018—Zimmer, H., Geometrical Optics, Applied Physics and Engineering, an International Series, vol. 9, 80 pages.

Exhibit 1019—Order Resetting Markman Hearing, 1 page.

Petition for Inter Partes Review of U.S. Pat. No. 10,905,333—IRP2021-01313, Case No. IPR2021-01313, U.S. Pat. No. 10,905,333, 76 pages.

IPR Institution Decision—IPR 2021-01313, U.S. Pat. No. 10,905,333 B2, Entered: Feb. 10, 2022, 43 pages.

IPR Institution Decision—IPR 2021-01312, U.S. Pat. No. 10,905,333 B2, Entered: Feb. 10, 2022, 43 pages.

Summons to attend oral proceedings pursuant to Rule 115(1) EPC) issued on Apr. 12, 2022, by the European Patent Office in corresponding European Application No. 13 809 950.2-1113, (7 pages).

* cited by examiner

3D INTRAORAL SCANNER MEASURING FLUORESCENCE

CROSS REFERENCE TO RELATED APPLICATIONS

The present application is a continuation of U.S. application Ser. No. 16/283,020, filed on Feb. 22, 2019, which is a continuation of U.S. application Ser. No. 16/264,835, filed on Feb. 1, 2019, which is a continuation of U.S. application Ser. No. 14/411,160, filed on Dec. 24, 2014, which is a U.S. national stage of International Application No. PCT/DK2013/050213, filed on Jun. 27, 2013, which is claims priority from U.S. Provisional Application No. 61/665,015, filed on Jun. 27, 2012 and Danish Application No. PA 2012 70382, filed on Jun. 29, 2012. The entire contents of each of U.S. application Ser. No. 16/283,020, U.S. application Ser. No. 16/264,835, U.S. application Ser. No. 14/411,160, International Application No. PCT/DK2013/050213, U.S. Application No. 61/665,015, and Danish Application No. PA 2012 70382 are hereby incorporated herein by reference in their entirety.

TECHNICAL FIELD

The invention relates to intraoral 3D scanning. In particular the invention relates to a 3D scanner system where fluorescence recorded from a patient's teeth is used for detecting cariogenic regions on the teeth. In particular the invention relates to a 3D scanner system where fluorescence recorded from the intraoral cavity is used when generating a digital 3D representation of the intra oral cavity.

BACKGROUND

US20080063998 describes a technique wherein one fluorescence image and one reflectance image are combined to form an image in which the contrast between a cariogenic region and a sound tooth structure is heightened in the 2D image.

US2008094631 describes a system with intraoral camera and measuring device. The measuring device is capable of collecting color, translucency, fluorescence, gloss, surface texture and/or other data for a particular tooth from the measuring device which then may be combined with images captured by intraoral camera.

Optical 3D scanners for recording the topographic characteristics of surfaces within the intraoral cavity, particularly of the dentition, are known in the prior art (e.g., WO2010145669). Examples of commercially available 3D intraoral scanners are 3Shape TRIOS, Cadent iTero, Sirona Cerec, and 3M Lava C.O.S.

The size of any probe element in intraoral scanners is limited because it has to fit into the human mouth. Accordingly, the field of view of such scanners is smaller than the object of interest in many applications, which can be multiple neighboring teeth or an entire dental arch. Hence, intraoral 3D scanners rely on "stitching" several sub-scans, each representative of a field of view, but obtained in multiple positions, e.g., by moving the 3D scanner along the dental arch. The 3D scanner records a series of sub-scans that are to be stitched to yield an overall digital 3D representation of the surface topography for the scanned part of the intraoral cavity. A sub-scan represents a depth map for a given relative position and orientation of the 3D scanner and the patient's intraoral cavity. To obtain multiple sub-scans, the 3D scanner is moved along the intraoral cavity or some region thereof and potentially also angled differently. The 3D scanner is to be moved and angled such that at least some sets of sub-scans overlap at least partially, in order to enable stitching. The result of stitching is a digital 3D representation of a surface larger than that which can be captured by a single sub-scan, i.e. which is larger than the field of view of the 3D scanner. Stitching, also known as registration, works by identifying overlapping regions of 3D surface in various sub-scans and transforming sub-scans to a common coordinate system such that the overlapping regions match, finally yielding the overall scan. The Iterative Closest Point (ICP) algorithm is widely used for this purpose.

SUMMARY

It is an object of the invention to provide a 3D scanner system which is capable of mapping fluorescence and/or a representation of a cariogenic region onto a digital 3D representation of the teeth.

It is an object of the invention to provide a 3D scanner system wherein the same image sensor is used for recording the probe light reflected from the teeth and the fluorescence emitted from fluorescent materials of the teeth, such as fluorescent materials in cariogenic regions of a tooth.

It is an object of the invention to provide a 3D scanner system wherein probe light reflected from the teeth and fluorescence emitted from fluorescent materials of the teeth, such as fluorescent materials in cariogenic regions of a tooth, can be read from the same recorded image.

Disclosed is a 3D scanner system for detecting and/or visualizing cariogenic regions in teeth based on fluorescence emitted from said teeth, said 3D scanner system comprising:
  an illumination unit capable of providing probe light for illuminating the teeth, where said probe light comprises light at a first wavelength which is capable of exciting a fluorescent material of the teeth;
  an image sensor for recording images of light received from the illuminated teeth, where said image sensor is capable of detecting fluorescence emitted from said fluorescent material when this is excited by light at said first wavelength;
  data processing means configured for:
    i. creating a digital 3D representation of the 3D topography of the teeth based on recorded images comprising probe light reflected from the teeth;
    ii. creating a representation of the fluorescence emitted from the fluorescent material of the teeth based on recorded images comprising the emitted fluorescence, and
    iii. mapping the representation of the emitted fluorescence onto the corresponding portion of the digital 3D representation of the teeth to provide a combined digital 3D representation; and
  a visual display unit on which the combined digital 3D representation is visualized.

In the visualization of the combined digital 3D representation the fluorescence and/or cariogenic regions are arranged according to their true position on the teeth. In some cases caries can be detected directly from the fluorescence emitted from the cariogenic region when illuminated by light at the first wavelength, such that the representation of the emitted fluorescence is a direct representation of the cariogenic region.

The mapped representation of an identified cariogenic regions may provide an improved visibility in relation to the tooth surface compared to how visible the identified cariogenic regions are on the tooth, such that the visualization of the combined digital 3D representation can provide valuable assistance to the dentist when examining a patient's set of teeth. This may e.g. be the case when the cariogenic region is represented with a distinct color and/or brightness in the combined digital 3D representation.

In the context of the present invention, the phrase "recording fluorescence" may refer to the case where fluorescence images showing fluorescence emitted from the fluorescent material are recorded.

The 3D scanner system according to the present invention has an illumination unit with at least a first light source that can emit light at a first wavelength intended to excite fluorescence materials in parts of the intraoral cavity, and an image sensor that can measure the fluorescence emitted from the fluorescent material when illuminated with light at said first wavelength. In some embodiments, the first light source provides UV light, and the fluorescence emitted from the fluorescent material in the hard dental tissue has a wavelength corresponding to visible light, such that standard image sensors can be used in the invention. Light sources useful in this invention can be lasers or LED's, or other.

A digital 3D representation of the 3D surface topography of an intraoral cavity can be generated based on light reflected from surfaces of the intraoral cavity. When a surface of the intraoral cavity is illuminated with light from a light source of the 3D scanner system the light reflected from the surface within a field of view is detected by an image sensor of the 3D scanner system. Based on the reflected light the data processing means can compute a sub-scan for the region of the surface arranged within the field of view. A series of sub-scans can be computed when e.g. a handheld part of the 3D scanner system is moved relative to the intraoral cavity such that different regions of the surface are arranged in the field of view.

The fluorescence emitted from the hard dental tissue may have a spectral distribution which depends on the wavelength of the light used to excite the fluorescent material, such that the fluorescence predominantly is within one wavelength range for one value of the first wavelength and within another wavelength range for another value of the first wavelength. The fluorescence may be emitted over a fluorescence wavelength range in which the fluorescent material emits fluorescence when excited by light at said first wavelength.

For measuring the 3D topographic characteristics of one or more surfaces of the intraoral cavity, the 3D scanner can employ any of the optical principles known in the art, e.g., focus scanning, confocal scanning, triangulation, or others. All these principles require at least one light source and measure some characteristic of the light reflected from the intraoral surface.

The image sensor is configured for recording the fluorescence emitted from the hard dental tissue when illuminated by light at the first wavelength, i.e. the image sensor allows the detection light at least at a wavelength which is larger than the first wavelength.

In some embodiments, the recording of the 3D topographic characteristics of utilizes reflections of the light at said first wavelength from the surfaces of the intraoral cavity. Some of the light at the first wavelength is reflected from the surfaces of the intraoral cavity while some is absorbed by fluorescent materials in the hard dental tissue.

In some embodiments, the image sensor is capable of detecting light at said first wavelength, such that the image sensor can detect both the fluorescence and light at the first wavelength. In this case, the image sensor can in addition to recording fluorescence from the hard dental tissue also be used for recording light at the first wavelength reflected from the surfaces of the intraoral cavity. The sub-scans for the surface can then be computed based on the recorded light at the first wavelength. The fluorescence and the reflected light can be distinguished either by the data processing means or by an optical filter. In the data processing means of a 3D scanner system utilizing a focus scanner configured for projecting a pattern of light onto the intraoral cavity surface, the fluorescence and the reflected light can be distinguished by a decomposition of the intensities recorded by the image sensor into the corresponding components.

In some embodiments, the fluorescence and the reflected light are distinguished by using an image sensor comprising a color filter array, such as a Bayer color filter array, and selecting the illumination unit such that it only provides probe light at a first wavelength in the blue part of the optical spectrum (e.g. at 405 nm). The blue pixels of the Bayer filter then allows reflected probe light to be recorded while the red and/or green pixels allows emitted fluorescence to be recorded such that the reflected probe light and the fluorescence can be recorded in the same image. The data processing means are then configured for reading the blue pixels on the recorded image only for creating the digital 3D representation of the teeth, and for reading the red/green pixels only for creating the fluorescence representation.

In some embodiments, the recording of the 3D topographic characteristics of the surface involves light at a second wavelength. The second wavelength may be such that light at the second wavelength mainly is reflected from the surfaces of the intraoral cavity with only a small fraction being absorbed by fluorescent materials in the hard dental tissue.

In some embodiments, the probe light comprises light at a second wavelength and the image sensor is capable of detecting light at said second wavelength, and where the digital 3D representation of the teeth is created based on light at the second wavelength in said images comprising probe light reflected from the teeth.

The absorption coefficient of the probe light in the teeth material may be 10 times weaker at the second wavelength than the first wavelength, such as 100 times weaker, such as 500 times weaker.

In some embodiments, the illumination unit is configured for providing light at the second wavelength for use in recording 3D topographic characteristics of the surface.

In some embodiments, the image sensor is capable of detecting light at said second wavelength, such that the image sensor can detect both the fluorescence and light at the second wavelength. In this case, the image sensor can in addition to recording fluorescence from the hard dental tissue also be used for recording light at the second wavelength reflected from the surfaces of the intraoral cavity. The sub-scans for the surface can then be computed based on the recorded light at the second wavelength.

In some embodiments, the wavelength of the emitted fluorescence is similar or identical to that used for recording the 3D topographic characteristics, such as similar or identical to the second wavelength. This is advantageous because the optical design can be simple, with little or no need to compensate for chromatic aberration.

An image sensor which is capable of detecting light at two different wavelengths and distinguishing between the two wavelengths can be realized by arranging a filter in front of the photodetectors of the image sensor, where some regions of the filter allows light at one wavelength to pass while other regions allow light at the other wavelength to pass. One configuration of such a filter could be a modified Bayer filter adapted to allow e.g. light at the first wavelength to pass to one known group of photodetectors and the fluorescence to pass to another known group of photodetectors in the image sensor.

In some embodiments, the 3D scanner system comprises a further image sensor. In some embodiments, the further image sensor is configured for detecting light at said first wavelength.

In some embodiments, the further image sensor is configured for detecting light at a second wavelength.

The image sensor or image sensors are arranged to capture light received from tissue of the intraoral cavity arranged within a field of view. The field of view is to some extent determined by the image sensor and the optical system of the 3D scanner system.

In some embodiments, the image sensor is configured for detecting light a wavelength range of 400 nm to 850 nm, such as in a range of 500 nm to 750 nm.

In some embodiments, the further image sensor is configured for detecting light within a wavelength range of 500 nm to 850 nm.

In some embodiments, the image sensor comprises an array of sensor elements, where at least a portion of the sensor elements are capable of detecting the emitted fluorescence.

This may e.g. be realized by using a color image sensor with a color filter array, such as a Bayer filter.

In some embodiments, the image sensor comprises a 2-dimensional detector, such as a 2D array of sensor elements.

In some embodiments, the image sensor comprises a 1-dimensional detector, such as a 1D array of sensor elements, and sweeping optics configured for imaging different portions of a surface onto this substantially 1-dimensional sensor element.

In some embodiments, the image sensor comprises a single sensor element and sweeping optics configured for imaging different portions of a surface onto this substantially 0-dimensional sensor element.

In some embodiments, the illumination unit is arranged to illuminate surfaces within the field of view, such that soft and hard dental tissue of the intraoral cavity of the intraoral cavity arranged within at least part of the field of view is illuminated. The illumination unit may be configured to illuminate surfaces covering an area which is part of the field of view, to illuminate surfaces covering an area substantially identical to the field of view, or to illuminate surfaces covering an area extending beyond the field of view.

In some embodiments, the illumination unit provides light in a first wavelength range, where said first wavelength is within said first wavelength range.

In some embodiments, the illumination unit further provides light in a second wavelength range, where said second wavelength is within said second wavelength range.

In some embodiments, the illumination unit comprises a first light source configured for providing said light at the first wavelength, such as configured for providing in a first wavelength range.

In some embodiments, the image sensor is capable of detecting light at said first wavelength, and wherein the digital 3D representation of the teeth is created based on light at the first wavelength in said images comprising probe light reflected from the teeth. In such cases the optical system of the 3D scanner system is designed to allow light at the first wavelength reflected from the teeth to be collected and guides to the image sensor.

In some embodiments, the color image sensor comprises a color filter array comprising a number of filters allowing light at said first wavelength to pass and a number of filters allowing the emitted fluorescence to pass, and where the data processing means bases at least part of the creating of the digital 3D representation of the teeth and at least part of the creating the representation of the fluorescence on the same recorded images.

In some embodiments, the multichromatic light source comprises a multi-die LED with an array of diodes emitting probe light at different wavelengths, such as an array of red, green and blue diodes.

In some embodiments, the illumination unit is capable of selectively activating only the subset of the LED diodes of the multi-die LED corresponding to the first wavelength while the image sensor only or preferentially reads out those pixels in the image sensor that have color filters at least approximately matching the color of the emitted fluorescence.

The subset of the dies preferably comprises one or more LED diodes which emits light at the first wavelength, which is within the excitation spectrum of the fluorescent teeth material, such as an ultraviolet, a blue, a green, or a yellow LED diode depending on the excitation spectrum of the fluorescent material.

In 3D scanner system comprising an illumination unit comprising an array of red, green and blue diodes, and an image sensor comprising a Bayer filter, the blue diodes of the illumination unit may be selectively activated during the fluorescence measurement, while the image sensor only reads the pixels that has color filters relating to green and/or red light. The light emitted from the subset of LED dies can then excite the fluorescent materials in the teeth and the scanner can record the fluorescence emitted from these fluorescent materials.

In some embodiments, the illumination unit is a single light source unit with only the first light source arranged to illuminate a surface of an intraoral cavity. In such cases the first light source is configured for providing light which can excite fluorescent material in the hard dental tissue and which can be reflected from the surfaces of the intraoral cavity such that sub-scans can be computed based in the reflected light. The emission spectrum of the first light source in such a single light source unit may be predominantly below 500 nm.

In some embodiments, the emission spectrum of the first light source is predominantly below 500 nm; the image sensor is capable of detecting light at said first wavelength, and the data processing means are configured for computing said sub-scans for the intraoral cavity surface/set of teeth from the detected light with said first wavelength, and for creating a digital 3D representation of the intraoral cavity surface/set of teeth by stitching said sub-scans. This allows for a single-light-source configuration where the first light source is used for both recording the 3D surface topography and the fluorescence.

In some embodiments, the illumination unit of the 3D scanner system only has a single light source, i.e. the first light source, and a filter configured for filtering the first wavelength used to excite fluorescence. This filter is arranged such that light received from the field of view must pass through the filter when propagating to the image sensor. One way to realize a filtering means is a dedicated optical filter, possibly one that can be moved into and out of the beam path.

In some embodiments, the first light source is capable of providing light at both said first and second wavelengths.

In some embodiments, the illumination unit comprises a second light source configured for providing said light at the second wavelength, such as configured for providing in a second wavelength range. In embodiments with two light sources, with different dominant wavelengths, the second light source is preferably used for recording the 3D topographic characteristics and the first light source is used for exciting the fluorescent material in the hard dental tissue.

In such a two-light source configuration, the first and the second light sources may be arranged at separate positions in the 3D scanner system. That is, the components of the illumination unit may be arranged separately in the 3D scanner system, such as separately in a handheld part of the 3D scanner system.

In some embodiments, the first light source is capable of providing light at both said first and wavelength and at a second wavelength, or the illumination unit comprises a second light source configured for providing said light at the second wavelength, such that the illumination unit is configured for providing light both at the first wavelength and at the second wavelength, while the image sensor is capable of detecting light at said second wavelength. The data processing means may then be configured for computing said sub-scans for the intraoral cavity surface/set of teeth from the detected light with said second wavelength and for creating a digital 3D representation of the set of teeth by stitching said sub-scans.

In some embodiments, the illumination unit is configured to provide light only at the first wavelength or only at the second wavelength at any time.

In some embodiments, the 3D scanner shifts between the two light sources repeatedly such that the surface of the intraoral cavity is illuminated successively by the light from the first and the second light source.

Tissue in the field of view of the 3D scanner system is then only illuminated by at most one of the first light source and the second light source at any time.

This can be realized by sequentially turning first and second light sources on and off, by providing that a first light source sequentially emits light at alternating wavelengths, or by blocking, directing, or selecting which of the first and second wavelengths are directed towards an exit point of the 3D scanner system.

In some embodiments, the 3D scanner system is configured such that only at most one of the first light source and the second light source provides light at any time. In some embodiments, the emission spectrum of said illumination unit and/or of said first light source is predominantly below 500 nm. This can be realized by an illumination unit which comprises only one light source whose emission spectrum is predominantly below 500 nm.

In the context of the present invention, an emission spectrum is said to be below or above a certain wavelength or within a certain range of wavelengths if a major portion of the light emitted from the illumination unit and/or from the first light source, such as such as more than 90%, such as more than 99%, or such as more than 99.9% of the light is below or above this wavelength or within this wavelength range.

In some embodiments, the first wavelength is in the range of 250 nm to 500 nm, such as in the range of 350 nm to 450 nm.

In some embodiments, the first light source is LED emitting blue or violet colored light which can be used for exciting fluorescent materials of teeth.

In some embodiments, the second wavelength is within a range of 500 nm to 850 nm. This can be realized by an embodiment comprising a second light source configured for providing light within this range. It can also be realized by an embodiment in which the first light source this is also is capable of emitting light at said second wavelength.

In some embodiments, the 3D scanner system comprises a dichroic mirror configured for having a larger reflection coefficient at said second wavelength than at wavelengths corresponding to the first wavelength and the fluorescence, wherein the dichroic mirror is arranged such that it guides light from the second light source towards surfaces arranged within the field of view and allows fluorescence received from the field of view to pass towards the image sensor.

In some embodiments, the dichroic mirror is arranged in the handheld part of the 3D scanner system.

In some embodiments, the field of view for the recording of the 3D surface topography of the teeth and the field of view for recording of fluorescence, respectively, are substantially identical.

In some embodiments, the field of view for the recording of images comprising probe light reflected and the field of view for recording of fluorescence, respectively, are substantially identical. This allows for simple and straightforward mapping of the fluorescence representation onto the digital 3D representation of the teeth created from the images comprising the reflected probe light.

In some embodiments, the 3D scanner system is configured to provide that a longer integration time is used when recording fluorescence compared to the integration time used for recording the reflected light from the surfaces of the intraoral cavity.

In some embodiments, the illumination unit, the image sensor and at least one unit of the data processing means are integrated parts of a handheld part of the 3D scanner system, such as handheld 3D scanner device. In embodiments comprising a first and a second light source, both light sources may be integrated parts of the handheld part of the 3D scanner system.

In some embodiments, the 3D scanner system comprises imaging optics for transmitting light received from one or more surfaces in the intraoral cavity to the image sensor when the 3D scanner is arranged in relation to the intraoral cavity.

In the context of the present invention, the phrase "3D scanner is arranged in relation to the intraoral cavity" describes a situation where the 3D scanning system is arranged such that it can illuminate at least one surface of the intraoral cavity and/or arranged such that light from the intraoral cavity can be received and recorded by the image sensor.

In embodiments, where the 3D scanner system comprises a handheld 3D intraoral scanner configured for engaging the intraoral cavity, the phrase describes a situation where the handheld 3D intraoral scanner is arranged such that it can receive light from the intraoral surfaces.

In some embodiments, the imaging optics is also configured for transmitting light from the illumination unit towards the surface of the intraoral cavity.

In embodiments, wherein the image sensor and the illumination unit are arranged in a handheld part of the 3D scanner system, the imaging optics may be an integrated part of the handheld part.

One way to realize a filtering means is to exploit that many optical materials have lower transmissivity for some wavelengths or an inherent sensitivity dependence on wavelength of the image sensor. Both effects are particularly noticeable when the light source emits deep blue or UV light.

In some embodiments, the filtering means are defined by the spectral properties of the optical elements of the imaging optics, such that the imaging optics provides the filtering function.

In some embodiments, the 3D scanner system comprises a control unit configured for controlling said illumination unit.

In some embodiments, the control unit is configured for controlling at which wavelength the first light source provides light at a given time.

In some embodiments, the control unit is configured for controlling the first light source such that the first light source alternatingly emits light at the first wavelength and at the second wavelength.

It can be advantageous to use a significantly higher intensity of the probe light for the excitation of the fluorescent tooth material than when recording the images for the 3D surface topography. Normally the intensity of the emitted fluorescence is much weaker than the intensity of light reflected from the tooth surface. By illuminating the tooth alternatingly with the light used for recording the 3D surface topography and the light used for exciting the fluorescence materials, the latter can be made more intense without saturating the image sensor by light reflected from the tooth surface.

In some embodiments, the control unit is configured for activating said first and second light sources in such a manner that the illumination unit sequentially emits light at said first and second wavelengths.

In some embodiments, the control unit is configured for controlling which of the first and the second light sources provide light at a given time. The control unit may e.g. be configured for sequentially turning on/off the first and second light sources in such a manner that only one of these light sources provides light to the field of view at any time.

In some embodiments, the control unit is configured for controlling optical components of the 3D scanner system such that light at the first and second wavelengths alternatingly is blocked, directed towards the field of view of the 3D scanner system, or selected to pass to illuminate a surface of an intraoral cavity.

The data processing means may consist of a single processor unit or of two or more sub-units, such that the function of the data processing means are divided by these sub-units.

In some embodiments, the data processing means is a single data processing unit configured for computing said sub-scans, for assigning said classification score and for said stitching.

In some embodiments, the data processing means comprises a number of sub-units, where one sub-unit is a data processing unit configured for computing said sub-scans, and another sub-unit is a data processing unit configured for assigning said classification score and for said stitching.

Such a single data processing unit or such a sub-unit may comprise a storage medium on which the appropriate algorithms are stored and a CPU configured for executing these algorithms.

In some embodiments, one sub-unit is arranged in a handheld part of the 3D scanner system and one or more sub-units are arranged in a remote part of the 3D scanner system, such as in a personal computer or a cart comprising a screen for visualizing the recorded 3D surface topography.

In some embodiments, the data processing means is capable of applying computer implemented algorithms configured for performing the computing of a series of sub-scans, the assigning of a classification score and the stitching of sub-scans. The data processing means may comprise one or more microprocessors capable of implementing such algorithms.

The data processing means may be capable of applying computer implemented algorithms configured for computing a series of sub-scans.

The data processing means may be capable of applying computer implemented algorithms configured for assigning classification scores.

The data processing means may be capable of applying computer implemented algorithms configured for stitching the sub-scans.

In some embodiments, the data processing means are configured for computing said sub-scans for the intraoral cavity surface from the detected light with said first wavelength. A series of sub-scans for surfaces of the intraoral cavity can then be computed based on light at the first wavelength reflected from the surfaces and detected by the image sensor or by the further image sensor.

In some embodiments, the data processing means are configured for computing said sub-scans for the intraoral cavity surface from the detected light with said second wavelength. A series of sub-scans for surfaces of the intraoral cavity can then be computed based on light at the second wavelength detected by the image sensor or by the further image sensor.

In some embodiments, the data processing means comprises a non-transitory computer readable medium having one or more computer instructions stored thereon, where said computer instructions comprises instructions for carrying out said algorithms.

In some embodiments, the 3D scanner system comprises means for filtering light reflected by surfaces in the intraoral cavity from the fluorescence emitted by the hard dental tissue.

The filtering means may provide a filtering of light at the first wavelength from the fluorescence emitted from the hard dental tissue when illuminated by light at the first wavelength.

The filtering means may provide a filtering of light at the second wavelength from the fluorescence emitted from the hard dental tissue when illuminated by light at the first wavelength.

Such a filtering may be advantageous in cases where the fluorescence emitted from the teeth is small compared to the intensity of the probe light. Filtering may then prevent saturation of the image sensor which otherwise may occur before a sufficiently strong fluorescence signal is recorded by the image sensor.

In some embodiments, the means for filtering comprises an optical filter which suppresses light at the first wavelength and/or light at the second wavelength more than it suppresses fluorescence emitted from the hard dental tissue when this is illuminated by light at said first wavelength. Such a filtering may be advantageous in cases where the fluorescence emitted from the teeth is small compared to the intensity of the probe light. Filtering may then prevent saturation of the image sensor which otherwise may occur before a sufficiently strong fluorescence signal is recorded by the image sensor.

In some embodiments, the filtering means provides a suppression of light at the first wavelength by more than about 3 dB, such as by more than about 10 dB, such as by more than about 20 dB, such as by more than about 30 dB.

Due to scattering and/or transmission loss in optical filters there may also be a slight suppression of the fluorescence in the optical filter. The optical filter may be configured to provide a filtering function in which the ratio between the suppression of light at said first or second wavelength and the suppression of the fluorescence is at least 5, such as at least 10, such as at least 50, such as at least 50, such as at least 100, such as at least 1000 or more.

In some embodiments the filtering means are implemented in the data processing means.

In some embodiments, the filtering means are configured for digitally decomposing the intensity of the signal detected by the image sensor into one component relating to the fluorescence and into one or more components relating to specular reflection, to diffuse reflection, and to stray light.

In some embodiments, the component relating to the specular reflection is used for recording the 3D surface topography or for creating the 3D digital representation of the set of teeth.

In some embodiments, the classification score for a given portion of the intraoral cavity is determined at least from the fluorescence recorded from this portion.

In general, it may be advantageous to use sub-scans covering large areas and without restrictive filtering out of subsets of data within a sub-scan, because the smaller surface area covered in sub-scans, the poorer the stitching. This is particularly true when the surface has little 3D structure.

When fluorescence is excited with light of wavelengths at which the 3D scanner system's image sensor is sensitive, for example near 400 nm, and no or non-perfect wavelength-discriminating optical filtering is applied, the image sensor will effectively record a sum of at least some emission and at least some reflection. A relatively stronger signal will thus be obtained from hard dental tissue, but some signal also from soft dental tissue.

In some embodiments, the representation of the emitted fluorescence is created by analyzing recorded images to identify sections of these images which correspond to fluorescence emitted from the teeth. This can be realized by selectively reading pixels of the image sensor which corresponds to the fluorescence emitted from the fluorescent teeth material when this is illuminated by probe light at said first wavelength.

In some embodiments, the representation of the fluorescence is a 2D representation and said mapping comprises folding the 2D fluorescence representation onto the digital 3D representation of the teeth.

Mapping the representation of the emitted fluorescence onto the corresponding portion of the digital 3D representation of the teeth may be defined as the adjustment of the fluorescence representation in relation with the digital 3D representation of the teeth, such that structures of the digital representations are coinciding. Thus common or alike structures of the 3D digital representation comprising geometrical data of the teeth and the digital fluorescence representation of the teeth are aligned.

Mapping to combine the digital representations may improve the visualization of a cariogenic region. In some embodiments, this is done by enhancing the visibility of the fluorescence representation by changing its color or brightness such that the fluorescence representation stands out more clearly in the visualized combined digital 3D representation.

In the context of the present invention, the phrase "visualizing the combined 3D representation" may refer to a visualization of all data provided by the combined 3D representation or to a visualization of a part of the data provided by the combined 3D representation. The visualized combined 3D representation may hence provide a visualization of the extracted information rather than all the data which can be provided from the 2D digital representation.

For a known geometry of the optical system of the 3D scanner system, such as the imaging optics and the illumination unit, and assuming no relative movement of the 3D scanner system and the intraoral cavity during the acquisition of images from which the sub-scan is computed and the fluorescence recording, a 2D image of fluorescence, which in essence is a texture, can be mapped/folded onto the digital 3D representation of the surface topography.

The mapping of 2D image data of fluorescence to the 3D surface in a sub-scan is particularly simple if both are obtained from the same view point and angle. In other words, it is beneficial for the 3D "depth image" and 2D fluorescence image to match by design. One way to implement such a design is to employ the same image sensor and imaging optics for recording the images on which the 3D reconstruction is based, and the images of fluorescence.

As fluorescence emission between sub-scans can differ, for example due to different distances to the teeth or due to different illumination angles, the images of fluorescence may need to be intensity-adjusted for the combined texture representing fluorescence on the entire 3D surface after stitching. For example, texture weaving can be employed to smooth intensity differences between different sub-scans (Callieri et al 2002).

In practice, the assumption of no relative movement of 3D scanner and intraoral cavity during the 3D surface and fluorescence recordings will generally not hold perfectly. In embodiments of this invention that switch been fluorescence and 3D surface recordings, there may be additional relative movement between those two phases.

In some embodiments, the representation of the fluorescence is a 3D representation and said mapping comprises registering the 3D fluorescence representation onto the digital 3D representation of the teeth.

The advantage of this is that in the combined digital 3D representation, the representation of the emitted fluorescence is arranged according to its true 3D position on the digital 3D representation of the teeth providing. A visualization of the combined digital 3D representation is hence accurate and allows e.g. a dentist to precisely identify which regions of the teeth are cariogenic.

In some embodiments, the data processing means are capable of mapping the recorded fluorescence onto the digital 3D representation of the intraoral 3D surface topography, such as by mapping a digital 3D representation of the fluorescence onto the digital 3D representation of the intraoral 3D surface topography.

The data processing means may comprise a storage medium on which algorithms for mapping the recorded fluorescence onto the digital 3D representation of the intraoral 3D surface topography are stored and a CPU configured for executing these algorithms.

In some embodiments, the 3D scanner system is capable of visualizing the mapped fluorescence on the digital 3D representation of the 3D surface topography. The 3D scanner system may comprise a visual display unit for visualizing and computer code for manipulating the graphical presentation on the visual display unit.

In some embodiments, the data processing means are configured for detecting differences in natural fluorescence of dentin and enamel. This may be detected using optical filters designed to distinguish between the fluorescence of the dentin and enamel, by recording the spectral distribution of the fluorescence or by digitally distinguishing between the between the fluorescence of the dentin and the fluorescence of the enamel.

In some embodiments, the 3D scanner system is capable of visualizing the differences in dentin and enamel on the digital 3D representation of the intraoral 3D surface topography. The 3D scanner system may be capable of providing a visual presentation of the digital 3D representation in which the dental and enamel can be distinguished by using e.g. different colors, textures, or opacities in the presentation or by allowing separate visualizations of the dentin and enamel to be controlled independently, e.g. by varying the transparency of the two independently.

In some embodiments, the data processing means are configured for detecting differences in fluorescence emitted from dental tissue, such as hard or soft dental tissue, and that emitted from dental equipment, such as a retraction cord.

In some embodiments, the 3D scanner system is capable of visualizing the differences in dental tissue and dental equipment on the digital 3D representation of the intraoral 3D surface topography. The 3D scanner system may be capable of providing a visual presentation of the digital 3D representation in which dental tissue and the dental equipment, can be distinguished by e.g. using different colors, textures, or opacities in the presentation or by allowing separate visualizations of the dental tissue and the dental equipment to be controlled independently, e.g. by varying the transparency of the two independently.

In some embodiments, the data processing means are configured for extracting information from the recorded fluorescence and for combining the extracted information with the digital 3D representation of the intraoral 3D surface topography.

In some embodiments, the 3D scanner system is capable of visualizing such as combination of the information extracted from the recorded fluorescence and the digital 3D representation of the intraoral 3D surface topography.

Fluorescence can also be exploited for diagnosis of some dental diseases.

Enamel demineralization and thus early caries can be detected by quantitative light-induced fluorescence (QLF), which uses light with wavelengths around 405 nm to excite yellow fluorescence at wavelengths above 520 nm (Angmar-Månsson and ten Bosch 2001). QLF has also been used to monitor tooth whitening (Amaechi and Higham 2001). Also pathogenic microflora can display fluorescence and be thus detected (Sinyaeva et al 2004).

Some embodiments of the 3D scanner system of this invention are capable of combining the benefit of more accurate stitching with that of a diagnostic function. It is particularly advantageous for the dentist that any diagnosed cariogenic region can be mapped onto the 3D representation of the teeth and visualized as such.

In some embodiments, the data processing means are configured for identifying cariogenic regions in which caries is present in more or less developed stages based on fluorescence detected from these areas.

In some embodiments, the 3D scanner system is configured for mapping a cariogenic region of a tooth onto the portion of the digital 3D representation of the 3D surface topography corresponding to said tooth.

The data processing means may be configured for providing a representation of the cariogenic region and mapping this representation onto the digital 3D representation of the 3D surface topography. The representation may involve a coloring of the cariogenic region such that the cariogenic region is clearly visible in a visualization of the digital 3D representation of the 3D surface topography with the mapped cariogenic region.

If teeth are illuminated with violet light in the spectrum of around 405 nm, it causes dentin to emit fluorescence. Cariogenic bacteria Streptococcus mutans produces special metabolites called porphyrins. These porphyrins fluoresce at red wavelengths, such as light in the wavelength range of 620-740 nm, when exposed to a 405-nm light, while healthy hard dental tissue fluorescence at green wavelengths, such as light in the wavelength range of 520-570 nm.

In some embodiments, the first wavelength is within the range of 375 nm to 435 nm, such as in the range of 385 nm to 425 nm, such as in the range of 395 nm to 415 nm, such as in the range of 400 nm to 410 nm.

In some embodiments the 3D scanner system is configured for deciding whether the fluorescence received from an illuminated portion of a tooth has a maximum intensity around 455 nm or in the range of 600 nm to 700 nm. This can be realized by using a color image sensor comprising a color filter array, such as the RGB filter array of a Bayer filter, and configuring the data processing means for comparing the readings in a recorded image such that the intensity of the blue pixels is compared to the intensity of the red pixels.

In general, a crude measure of the spectral distribution of the emitted fluorescence can be realized by using a color image sensor comprising a color filter array, such as the RGB filter array of a Bayer filter. The pixels of the recorded image each belong to one of the colors of the filter. The data processing means are then configured for comparing the readings in the different pixels in a recorded image and from that determine the ratio between e.g. the blue, green and red components of the emitted fluorescence.

When sound teeth are illuminated by light with a wavelength of 405 nm the teeth emits fluorescence with a broad emission at 500 nm that is typical of natural enamel, whereas in caries teeth additional peaks are seen at 635 and 680 nm due to emission from porphyrin compounds in oral bacteria.

In some embodiments, the 3D scanner system is configured for deciding whether the fluorescence received from an illuminated portion of a tooth has peaks in the range of 600 nm to 700 nm.

In some embodiments, the 3D scanner system is configured for deciding whether the fluorescence received from an illuminated portion of a tooth has a maximum intensity around 455 nm or around 500 nm.

The deciding may be realized by optical components arranged to separate light at the wavelengths.

The deciding may be realized by using a color image sensor with a Bayer color filter array as the image sensor of the 3D scanner system and reading the ratio between the signals from the blue and green pixels of the image. In such a design, the green to blue ratio is significantly larger for the 500 nm fluorescence than at 455 nm.

In some embodiments, the data processing means are capable of detecting a local decrease in the natural fluorescence of a tooth caused by scattering due to a caries lesion.

In some embodiments, a data processing means are capable of implementing a data analysis in which the spectral properties of the recorded images are taken into account.

A particular problem with stitching of intraoral sub-scans is soft tissue in the oral cavity that moves between sub-scans and even within a sub-scan. Overlapping regions in multiple sub-scans may therefore not be identified correctly, deteriorating the quality of the stitching algorithm's result. In contrast, the parts of the sub-scans that represent rigid objects such as teeth or prostheses, but also rugae in the anterior palate, potentially allow better stitching.

Only hard dental tissue emits fluorescence when illuminated by a light source (Hartles 1953). The present invention utilizes this fact to differentiate between hard and soft dental tissue in an intraoral cavity, such that the soft and hard dental tissues may be assigned different weights in the stitching of sub-scans to provide a digital 3D representation of the intraoral cavity. The differentiation of the hard and soft tissue can be such that the hard dental tissue is assigned a higher weight that the soft dental tissue, such that potential errors in the stitching due to e.g. movement or deformation of the soft tissue are mitigated.

The 3D scanner of the present invention is hence configured to measure the natural fluorescence of hard dental tissue in addition to the 3D topographic characteristics of one or more surfaces of the intraoral cavity, and to differentiate between the soft and hard dental tissue in the stitching of sub-scans based on this fluorescence.

Disclosed is hence a 3D scanner system for recording a 3D surface topography of a patient's intraoral cavity based on a series of sub-scans, the intraoral cavity comprising soft dental tissue and hard dental tissue, said 3D scanner system comprising:

an illumination unit configured for providing light at a first wavelength, where light at said first wavelength can excite fluorescent material of the hard dental tissue;

an image sensor configured for recording fluorescence emitted from the fluorescent material when this is excited by light at said first wavelength; and data processing means for:
  i. computing sub-scans for the intraoral cavity surface, each sub-scan representing a depth map of a region of said intraoral cavity surface topography as seen from a given position and orientation relative to said surface;
  ii. assigning classification scores to portions of said sub-scans relating to the hard dental tissue and to the soft dental tissue, where said classification score differentiates between the hard dental tissue and the soft dental tissue, and where said classification score at least partly is based on the recorded fluorescence; and
  iii. stitching said sub-scans to create a digital 3D representation of the intraoral 3D surface topography, where the hard and soft dental tissues are weighted differently in the stitching based on said classification scores.

Disclosed is a method for recording a 3D surface topography of a patient's intraoral cavity based on a series of sub-scans, the intraoral cavity comprising soft dental tissue and hard dental tissue, said method comprising:

obtaining a 3D scanner system according to any of the embodiments;

scanning at least a part of the intraoral cavity using said 3D scanner system and computing sub-scans relating to a number of scanned regions of the intraoral cavity, each sub-scan representing a depth map of a region of said intraoral cavity surface topography as seen from a given position and orientation relative to said surface;

assigning classification scores to portions of said sub-scans relating to the hard dental tissue and to the soft dental tissue, where said classification score differentiates between the hard dental tissue and the soft dental tissue, and where said classification score at least partly is based on fluorescence recorded using said 3D scanner system;

stitching said sub-scans to create a digital 3D representation of the intraoral 3D surface topography, where the hard and soft dental tissues are weighted differently in the stitching based on said classification scores.

Fluorescence of dentin and enamel has been observed to differ in strength at least for some excitation or observation wavelengths (Hartles 1953). By the same principle as the differentiation between hard and soft dental tissue, this phenomenon can be exploited to differentiate the two materials. In particular, it can be exploited to detect a preparation line, which is particularly important to know when dental restorations are to be designed and manufactured.

The dentist often prepares a tooth below the gingival. This results in the soft tissue wrapping around the sub-gingival preparation line and hinders scanning. To remedy this and allow for a clear view of the preparation line the dentist can surround the prepared tooth by retraction cord. Such retraction cord can be made to fluoresce much more brightly than hard tissue in the oral cavity by addition of fluorophores. Such bright fluorescence can be exploited to detect preparation lines, which is particularly important to know when dental restorations are to be designed and manufactured.

The soft dental tissue of the intraoral cavity may comprise gingiva, buccal tissue, tongue, or the tissue of the anterior palette.

The hard dental tissue of the intraoral cavity may comprise natural teeth, the dentin or the enamel of a tooth, or a dental restoration.

While the 3D surface recording function of the 3D scanner system is based on reflection from the surface which records both hard and soft tissues, only the hard dental tissues emits fluorescence (Hartles 1953). Some dental restorations have also been observed to emit fluorescence when illuminated. This is advantageous because they too represent rigid structures and thus valuable input for the stitching operation. In the sense of this invention, fluorescing dental restorations may thus be considered equivalent with dental hard tissue.

In some embodiments, the data processing means are configured to provide that the differentiation between hard and soft dental tissue and/or the assignment of classification scores to the hard and soft dental tissue is also based on the 3D topographic characteristics of the surface.

In some embodiments, the data processing means applies computer implemented algorithms configured for stitching said sub-scans, where said algorithms are configured for taking into account both information derived from light reflected from the surface of the illuminated regions of the surface of the intraoral cavity and information derived from the fluorescence emitted from the excited fluorescent materials in the hard dental tissue in these portions.

Some soft tissue in the oral cavity, particularly at the anterior palate, is in fact rather rigid, and even more advantageously for the purpose of stitching, it has a clear 3D structure, the rugae. It can thus be advantageous to not only differentiate tissue types by fluorescence (or, as in U.S. Pat. No. 7,698,068, by color), but also by structure. Rugae can for example be detected due to their approximately known 3D surface structure. For some orthodontic appliances, knowledge of the 3D geometry of the palate is important, so an intraoral 3D scanner should preferably be able to record it.

In some embodiments, the classification score relates to a probability of belonging to a class of soft dental tissue or a class of hard dental tissue.

In some embodiments, the classification score further divides soft dental tissue into soft tissue sub-classes, such as gingiva, buccal tissue, tongue, rugae in the hard anterior palette.

An advantage of further dividing the soft tissue is that the position of some types of soft tissue relative to the other parts of intraoral cavity is relatively fixed. The anterior palette e.g. cannot move as much as the tongue.

In some embodiments, the classification score further divides hard dental tissue into hard tissue sub-classes, such as natural teeth, dental restorations, the dentin or the enamel of a tooth.

The data processing means may then be configured for assigning a probability for a portion of the sub-scans of belonging to a given soft tissue sub-class.

The data processing unit may then be configured for assigning a probability for a portion of the sub-scan of belonging to a given hard tissue sub-class.

In some embodiments, the data processing means are configured for assigning a classification score to equipment used in a dental procedure, such as a retraction cord placed in the intraoral cavity by e.g. a dentist during a dental procedure.

In some embodiments, the classification score comprises a numerical value.

The classification score and the weighting of sub-scans based on this classification score may be such that a relatively higher numerical value indicates that the corresponding portion is weighted higher in the stitching.

The classification score and the weighting of sub-scans based on this classification score may be such that a relatively lower numerical value indicates that the corresponding portion is weighted higher in the stitching.

In some embodiments, the relative value of the classification scores for two portions of a sub-scan relating to different classes or sub-classes of dental tissue determines the relative weight these two portions have in the stitching.

In some embodiments, the classification scores for hard and soft dental tissue are such that hard dental tissue is weighted higher than soft dental tissue in the stitching.

In some embodiments, the classification scores for rugae of the anterior palette and other kinds of soft dental tissue, such as the buccal tissue and the tongue, are such that said rugae is weighted higher than the other kinds of soft dental tissue in the stitching.

This provides the advantage that the stitching of sub-scans can be improved compared to when all soft tissue is weighted equally.

In some embodiments, the weighting is such that hard dental tissue has a weight which is 5 times higher than the soft dental tissue, such as 10 times higher, such as 15 times higher, such as 25 times higher, such as 50 times higher, such as 75 times higher, such as 100 times higher or even more.

In some embodiments, utilizing an iterative closest point procedure, the local distance between corresponding portions of two point clouds is multiplied with the classification score such that a distance is weighted highly for a high classification score and a distance has a low weight for a low classification score.

In some embodiments, the relative weighting of the different regions is given by a linear relationship:

$$w_{n,m} = k_1 c_{n,m} + k_2$$

where n is a label identifying a scanned surface element, m is the sub-scan label, $w_{n,m}$ is the weight used for surface element n in the stitching of sub-scan m to create the 3D representation of the intraoral 3D surface, $c_{n,m}$ is the fluorescence dependent signal recorded for surface element n in sub-scan m, and $k_1$ and $k_2$ are constants determined before the scanning.

In some embodiments, the relative weighting of the different regions is given by a second order polynomial where a second order term is added:

$$w_{n,m} = k_1 (c_{n,m})^2 + k_2 c_{n,m} + k_3$$

where the constants $k_1$, $k_2$, and $k_3$ are determined before the scanning.

In some embodiments, the relative weighting of the different regions is given by a more general expression:

$$w_{n,m} = f(n, c_m)$$

where $c_m$ is the collection of all fluorescence dependent signals recorded for sub-scan m. This more general expression includes schemes where edges or gradients in the fluorescence-dependent signal are used in assigning soft/hard tissue classification in surface element n.

The relative weighting may be described by a step function where the different classes of tissue a taken into account if their classification score is above a certain threshold value.

Because of all the above described uncertainties with differentiating soft and hard tissue, and because of the benefits of recording at least part of the soft tissue, it is not advisable to completely ignore supposed, but in actuality misclassified, soft tissue in the stitching. U.S. Pat. No. 7,698,068 according to its claim 1, in contrast, teaches to stitch sub-scans based on "only a first portion" thereof, i.e., to perform a complete and fully discriminating segmentation of the 3D surface data by color before stitching. This invention, in contrast, holds that it is advantageous to assign the supposed soft tissues a smaller, but non-zero weight in the stitching algorithm. Many such standard algorithms, e.g., ICP, are based on sum of some norm of distance deviations between regions of sub-scans, and can simply be extended to weighted sums, for example a weighted sum of squared distances.

In some embodiments, the data processing means are configured for taking into account the risk of assigning a false classification score of a portion of the intraoral cavity.

It can also be advantageous to detect hard tissue not only from fluorescence, but at least partly also based on 3D surface structure. For example, canine, premolar, and molar teeth have an at least approximately known occlusal surface with a number of cusps.

In some embodiments, the classification score for a given portion of the intraoral cavity is determined at least partly from an identification of the portion based on the surface topography is this portion. The identified portion of the intraoral cavity may relate to a canine, a premolar, or a molar tooth. An example of a suitable algorithm for making such identification is described in Kronfeld et al 2010. The rugae of the anterior palette with its characteristic surface modulation can also be used for this purpose.

For some applications of a 3D scanner system it is advantageous to provide a higher precision and/or spatial resolution for a region of particular interest. The region of particular interest can be marked in the intraoral cavity using dental equipment, such as a retraction cord arranged to at least partially surround the region. Based on the fluorescence emitted from it, the dental equipment can be identified in a sub-scan or in the stitched digital 3D representation of the intraoral 3D surface topography such that its location relative to the dental tissue can be determined. When the dental equipment marks a boundary between the region of particular interest and the remaining regions of the intraoral cavity knowledge of its location can be used for automatically identifying the region of particular interest in the created digital 3D representation.

Disclosed is hence a 3D scanner system for recording a 3D surface topography of a patient's intraoral cavity based on a series of sub-scans acquired with dental equipment arranged in the intraoral cavity, where the dental equipment comprises a fluorescent material which emits fluorescence when illuminated by light at a first wavelength, said 3D scanner system comprising:

an illumination unit configured for providing light at said first wavelength;

an image sensor configured for recording fluorescence emitted from the fluorescent material when this is excited by light at said first wavelength; and data processing means for:
  i. computing sub-scans for the intraoral cavity surface, each sub-scan representing a depth map of a region of said intraoral cavity surface topography as seen from a given position and orientation relative to said surface;
  ii. stitching said sub-scans to create a digital 3D representation of the intraoral 3D surface topography; and
  iii. identifying the dental equipment in a sub-scan or in the stitched digital 3D representation of the intraoral 3D surface topography and determining the position of the dental equipment relative to the dental tissue based on recorded fluorescence emitted from the dental equipment.

In some embodiments, the settings of the 3D scanning, such as the number of images acquired for the computation of each sub-scan, can be adjusted during a 3D scanning. With an appropriate change of the settings sub-scans with a higher precision and/or resolution can be obtained for selected regions, such as for a region of particular interest.

The region of particular interest may e.g. relate to a prepared tooth for which a dental restoration is to be designed based on the digital 3D representation of the intraoral 3D surface topography.

In some embodiments, the data processing means are configured to provide that when the dental equipment is arranged such that it marks a boundary between a region of particular interest and the remaining regions of the intraoral cavity, the data processing means are capable of identifying the portion of the digital 3D representation corresponding to the region of particular interest based on the fluorescence from the dental equipment recorded by the image sensor.

In some embodiments, the data processing means are capable of deriving a virtual model of the dental equipment based on the fluorescence recorded from the dental equipment, and where the position of the boundary in the digital 3D representation is determined based on this virtual model.

In some embodiments, deriving the virtual model of the dental equipment comprises matching the fluorescence recorded from the dental equipment with a template virtual model from a dental equipment library.

In some embodiments, the identification of the region of particular interest also is based on an analysis of the recorded 3D surface topography.

In some embodiments, the 3D scanner system is capable of adjusting the settings relating to the precision and/or spatial resolution at which the 3D scanner system acquires data from surface for computing the sub-scans, such that a higher precision and/or resolution can provided for the region of the digital 3D representation corresponding to the region of particular interest.

In some embodiments, the method is such that the classification score differentiates between different sub-classes of hard dental tissue, such as natural teeth, dental restorations, dentin/enamel and/or wherein said classification score further differentiates between different sub-classes soft dental tissue, such as gingiva, buccal tissue, tongue, rugae in the hard anterior palate.

In some embodiments, the method is such that the assigned classification score relates to a probability for a portion of a surface in a given sub-scan to belong to a given soft dental tissue class, soft dental tissue sub-class, hard dental tissue class, or hard dental tissue sub-class.

In some embodiments, the method is such that the assigned classification score is a numerical value indicating the weight of the portion in the stitching of the sub-scans.

In some embodiments, the method comprises determining a preparation line based on differences in the fluorescence emitted from the dentin and the enamel of a prepared tooth.

In some embodiments, the 3D scanner system comprises a handheld part and wherein said handheld part is moved relative to said intraoral cavity between acquisitions of different sub-scans.

Disclosed is a 3D scanner system for detecting caries in teeth of a patient's intraoral cavity, said 3D scanner system comprising:

an illumination unit configured for providing light at a first wavelength, where light at said first wavelength can excite fluorescent material of the teeth;

an image sensor configured for recording fluorescence emitted from the fluorescent material when this is excited by light at said first wavelength;

data processing means for:
  i. creating a digital 3D representation of the patient's set of teeth;
  ii. analyzing the recorded fluorescence to identify cariogenic regions of the teeth;
  iii. creating a representation of identified cariogenic regions; and
  iv. mapping the representation of identified cariogenic regions onto the corresponding portion of the digital 3D representation of the teeth to provide a combined digital 3D representation; and a visual display unit on which the combined digital 3D representation can be visualized.

Disclosed is a 3D scanner system for detecting caries in teeth of a patient's intraoral cavity based on a series of sub-scans, said 3D scanner system comprising:

an illumination unit configured for providing light at a first wavelength, where light at said first wavelength can excite fluorescent material of the teeth;

an image sensor configured for recording fluorescence emitted from the fluorescent material when this is excited by light at said first wavelength;

data processing means for:
  i. computing sub-scans for the intraoral cavity surface, each sub-scan representing a depth map of a region of said intraoral cavity surface topography as seen from a given position and orientation relative an intraoral cavity surface;
  ii. stitching said sub-scans to create a digital 3D representation of the patient's set of teeth;
  iii. analyzing the recorded fluorescence to identify cariogenic regions of the teeth; and iv. mapping cariogenic regions onto the corresponding portion of the digital 3D representation of the teeth to provide a combined digital 3D representation in which the cariogenic regions are arranged according to their true position on the teeth; and a visual display unit on which the combined digital 3D representation can be visualized.

3D modeling is the process of developing a mathematical, wireframe representation of any three-dimensional object, called a 3D model, via specialized software. Models may be created automatically, e.g. 3D models may be created using multiple approaches: use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

The intra-oral scanner may be configured for utilizing focus scanning, where the digital 3D representation of the scanned teeth is reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

The present invention relates to different aspects including the system and method described above and in the following, and corresponding systems and methods, each yielding one or more of the benefits and advantages described in connection with the first mentioned aspect, and each having one or more embodiments corresponding to the embodiments described in connection with the first mentioned aspect and/or disclosed in the appended claims.

Disclosed is a 3D scanner system for recording a 3D surface topography of a patient's intraoral cavity based on a series of sub-scans, the intraoral cavity comprising soft dental tissue and hard dental tissue, said 3D scanner system comprising:

an illumination unit configured for providing light at a first wavelength, where light at said first wavelength can excite fluorescent material of the hard dental tissue;

an image sensor configured for recording fluorescence emitted from the fluorescent material when this is excited by light at said first wavelength;

means for generating a series of sub-scans for the intraoral cavity surface based on the light captured by the image sensor, where each sub-scan represents a depth map as seen from a given position and orientation relative to the intraoral cavity surface; and a data processing means for:
at least partly differentiating dental hard and soft tissue based on fluorescence emitted from fluorescent material in the hard dental tissue, and for stitching said sub-scans to create a digital 3D representation of the intraoral 3D surface topography, where the hard and soft dental tissues are weighted differently in the stitching.

In some embodiments, the different weighting in the stitching is based on the result of the differentiating of hard and soft tissue.

According to an aspect of the invention is a 3D scanner system for recording a 3D surface topography of a patient's intraoral cavity based on a series of sub-scans, the intraoral cavity comprising soft dental tissue and hard dental tissue, said 3D scanner system comprising:

an illumination unit configured for providing light at a first wavelength, where light at said first wavelength can excite fluorescent material of the hard dental tissue;

an image sensor configured for recording fluorescence emitted from the fluorescent material when this is excited by light at said first wavelength; and data processing means for:
i. computing sub-scans for the intraoral cavity surface, each sub-scan representing a depth map of a region of said intraoral cavity surface topography as seen from a given position and orientation relative to said surface;

ii. assigning classification scores to portions of said sub-scans relating to the hard dental tissue and to the soft dental tissue, where said classification score differentiates between the hard dental tissue and the soft dental tissue, and where said classification score at least partly is based on the recorded fluorescence; and iii. stitching said sub-scans to create a digital 3D representation of the intraoral 3D surface topography, where the hard and soft dental tissues are weighted differently in the stitching based on said classification scores.

According to an aspect of the invention is a method for recording a 3D surface topography of a patient's intraoral cavity based on a series of sub-scans, the intraoral cavity comprising soft dental tissue and hard dental tissue, said method comprising:

obtaining a 3D scanner system according to any of the embodiments;

scanning at least a part of the intraoral cavity using said 3D scanner system and computing sub-scans relating to a number of scanned regions of the intraoral cavity, each sub-scan representing a depth map of a region of said intraoral cavity surface topography as seen from a given position and orientation relative to said surface;

assigning classification scores to portions of said sub-scans relating to the hard dental tissue and to the soft dental tissue, where said classification score differentiates between the hard dental tissue and the soft dental tissue, and where said classification score at least partly is based on fluorescence recorded using said 3D scanner system;

stitching said sub-scans to create a digital 3D representation of the intraoral 3D surface topography, where the hard and soft dental tissues are weighted differently in the stitching based on said classification scores.

According to an aspect of the invention is a 3D scanner system for detecting caries in teeth of a patient's intraoral cavity, said 3D scanner system comprising:

an illumination unit configured for providing light at a first wavelength, where light at said first wavelength can excite fluorescent material of the teeth;

an image sensor configured for recording fluorescence emitted from the fluorescent material when this is excited by light at said first wavelength;

data processing means for:
  i. creating a digital 3D representation of the patient's set of teeth;
  ii. analyzing the recorded fluorescence to identify cariogenic regions of the teeth;
  iii. creating a representation of identified cariogenic regions; and
  iv. mapping the representation of identified cariogenic regions onto the corresponding portion of the digital 3D representation of the teeth to provide a combined digital 3D representation; and a visual display unit on which the combined digital 3D representation can be visualized.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

The figures below illustrate schematically how embodiments of a 3D scanner according to this invention can be realized. The figures are not necessarily dimensionally precise.

Figure 1:
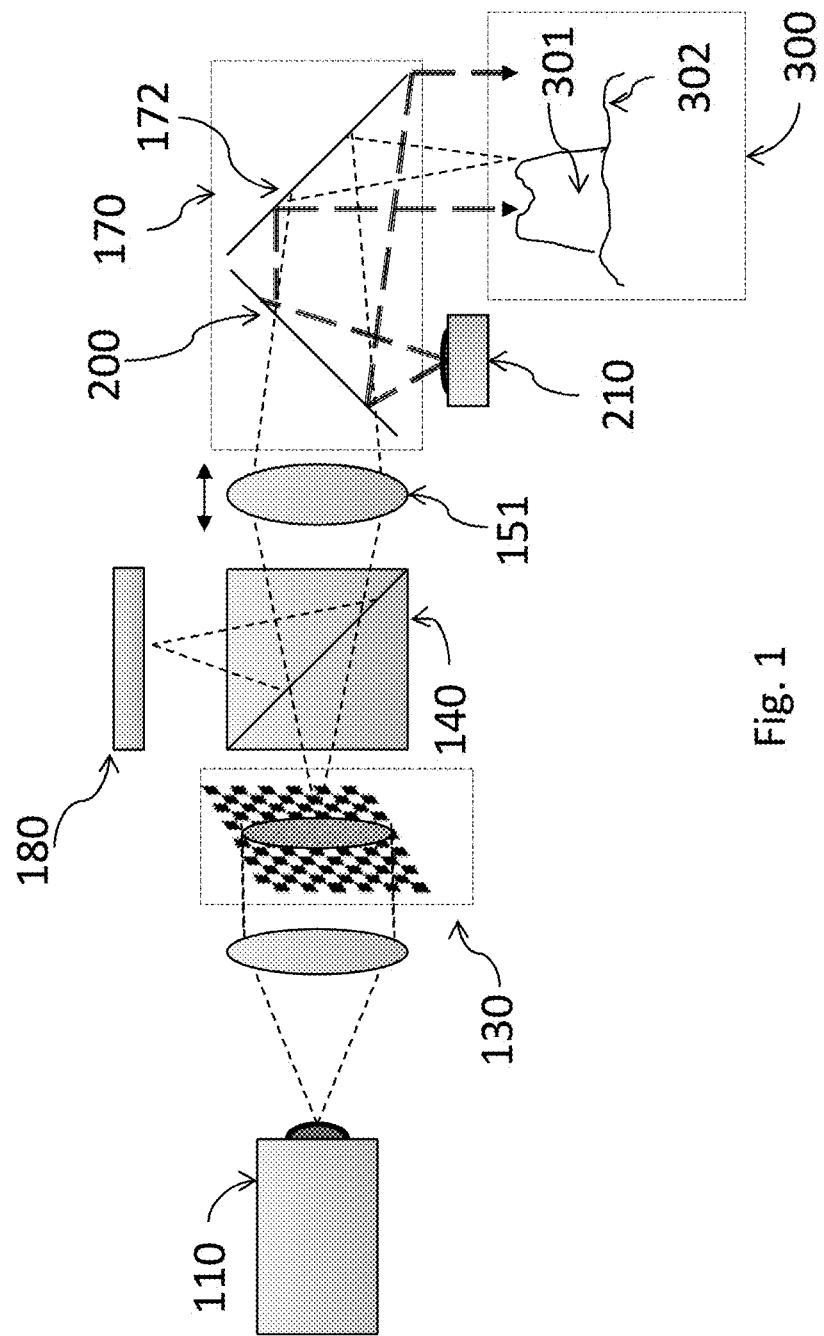
FIG. 1 shows an embodiment of the 3D scanner system according to the present invention.

FIG. 1 shows an embodiment of the invention, namely a focus scanning intraoral 3D scanner comprising an illumination unit with a first light source 210 and a second light source 110, a pattern 130 (a line in a true cross-sectional view, but shown here at an angle for clarity), an image sensor 180, a beam splitter 140, and focusing optics with a moveable lens 151. The 3D scanner has a tip or probe 170 with a mirror 172 that folds the beam path towards the region of the intraoral cavity being scanned 300. The intraoral cavity comprises hard dental tissue 301 and soft dental tissue 302. The second light source 110 emits light at least at the second wavelength and may comprise collimation optics. In the figure, the short thin dashed lines illustrate light rays emitted from the second light source and imaged through the optical system onto the object being scanned, returned through the optical system, and light rays imaged onto the image sensor. The 3D surface topography of the patient's intraoral cavity is recorded based on images acquired with the image sensor when the object is illuminated with light from the second light source. The second light source 110 is thus intended for 3D surface recording, and the first light source 210 may be turned off during 3D surface recording.

The 3D scanner can include other elements as well; however they are not essential for this invention and are not illustrated in the figure. A detailed description of a focus scanning device including other potentially beneficial elements and the associated calculations is given in WO2010145669.

The first light source 210 of the illumination unit of the embodiment shown in FIG. 1 is configured for emitting light at the first wavelength intended to excite fluorescence in the hard tissue parts of the intraoral cavity 300. A dichroic mirror 200 directs the light from the first light source 210 towards mirror 172. The dichroic mirror 200 is transmissive to the wavelengths generated by the second light source 110 and fluorescence from the hard tissue 301, but reflective to those generated by the first light source 210. Mirror 172 is reflective at wavelengths generated by the first and second light sources 110, 210, and fluorescence from the hard tissue 301. Light rays emitted by the first light source 210 are illustrated as lines with thick, long dashes. The light at the first wavelength excites fluorescence in the hard tissue parts 301. A portion of the emitted fluorescence follows the substantially same path as the light from the second light source 110 after it is reflected from the dental cavity, such that this portion of the emitted fluorescence can be directed towards the image sensor 180 by the beam splitter 140.

The first light source 210 can be a LED with an emission peak at 405 nm, and the second light source 110 can be an LED with an emission peak above 520 nm, for example at 590 nm.

As indicated by the double-sided arrow in FIG. 1, during a 3D scan the focus of the optical system is swept from one end of the focus volume to the other end by moving the focus lens 151 in the direction along the main optical axis. The focus sweep translates the focus in a direction substantially along the optical axis of the optical system. During the focus sweep a stack of images is obtained with the image sensor 180.

As described in WO2010145669, a correlation measure A, within a block of pixels representing one region of the checkerboard pattern shown in FIG. 1 can be determined by means of the following formula:

$$A = \sum_{i=1}^{n} f_i I_i = f \cdot I$$

where n is the number of pixels within the block, f is the reference signal vector obtained from knowledge of the pattern configuration after a calibration, and I is the input signal vector, i.e., the intensities recorded in the pixels. The block can be a square block of pixels covering the image of at least one period of the checkerboard pattern, for example n=2×2 or n=4×4 or n=6×6. The 3D coordinates for each such block are then determined from the location of the maximum of A over the series of images in a focus sweep. Note that with the above method, the 3D coordinates of both hard tissue 301 and soft tissue 300 are found. For the details of the calculations including a method to find f, see again WO2010145669.

In the embodiment illustrated in FIG. 1, the image sensor 180 can also be used for measuring fluorescence, i.e., the light emitted by the dental hard issue after excitation. In this mode, the second light source 110 is turned off, while the first light source 210 is turned on. In particular a focus scanner is characterized by a shallow depth of focus, and hence a single image will not be sharp over the range of depths typically encountered in a view of the intraoral cavity. One way to obtain a sharp image over all locations of the focus planes during a sweep is to generate a "fused image" that combines the sections that are optimally in focus from all images taken during a sweep.

A detailed description of how this step may be performed is illustrated in FIG. 17 and the associated text of WO2010145669. The recording of an image of fluorescence can be based on an entire sweep of the focus lens, just like the acquisition of a 3D sub-scan. It may also be admissible for some applications to accept imperfect sharpness of the fluorescence image, and only take a few images of fluorescence during the sweep, for example when the focus lens is at its extreme positions, and to "fuse" those as described in WO2010145669.

It may be advantageous to increase exposure time of the image sensor when fluorescence is recorded. This is so because the intensity of the fluorescence-emitted light can be smaller than that of the reflected 3D-recording light, i.e., when the second light source 110 is on. If the speed of the focus lens is the same as during 3D surface recording, a longer exposure time results in fewer images taken during a sweep, and hence the "fused" image is less sharp. Alternatively, the speed of the focus lens can be reduced, which from optical reasoning should give sharper "fused" images, but in actuality comes at a risk of loss of sharpness due to hand or patient movement during the relatively longer sweep.

The intensity of the fluorescence image can be used as a relative weight in the stitching algorithm, expressing the level of certainty in the classification as hard dental tissue. Note that the stitching images present all pixels of the sensors, whereas the 3D coordinates are computed for a block of pixels according to equation (1). Thus, it can be advisable to find an average intensity for the corresponding pixel block in the fluorescence image and associate that with the 3D coordinate found for the pixel block.

Figure 2:
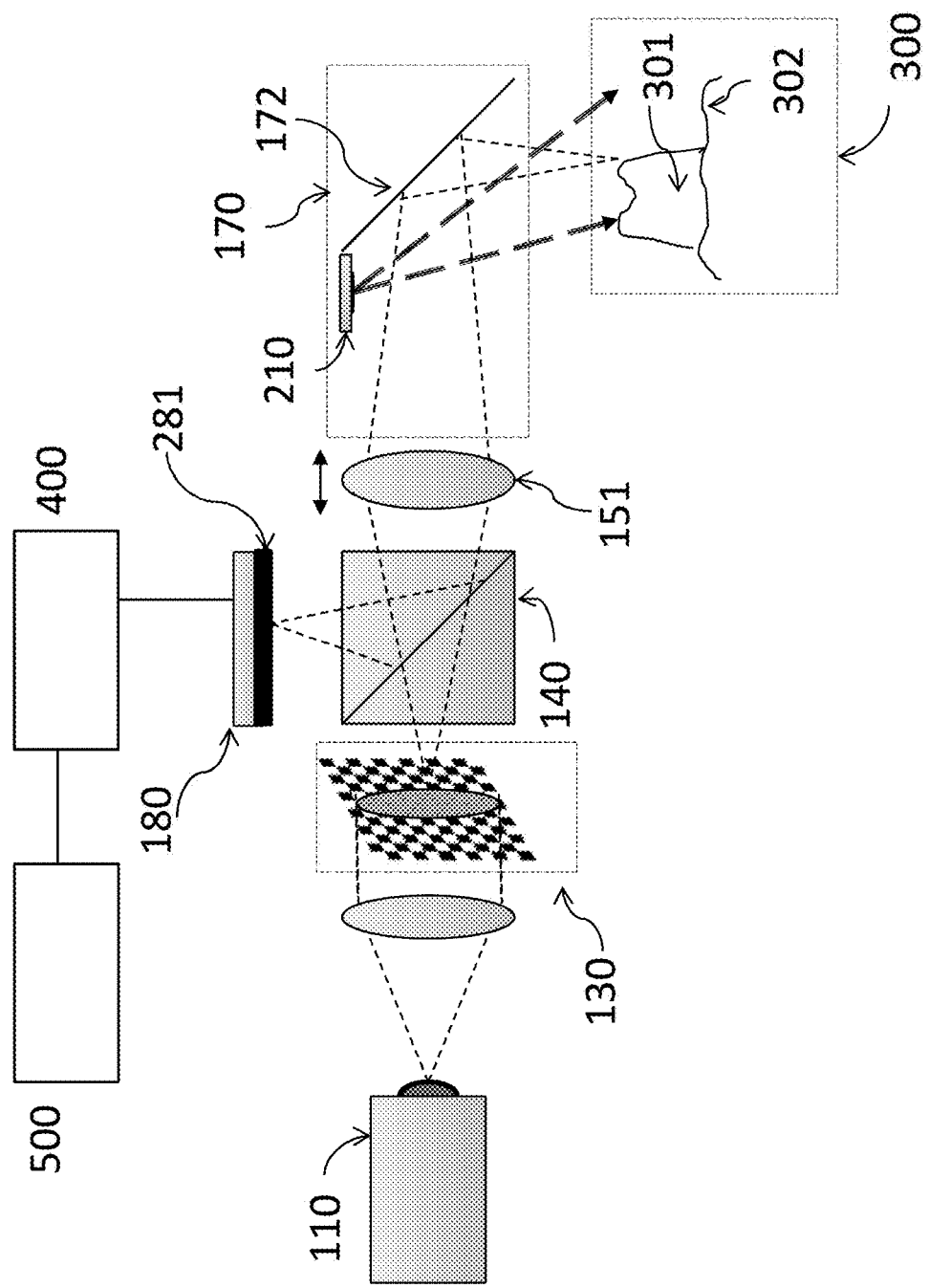
FIG. 2 shows an embodiment of the 3D scanner system according to the present invention with the first light source is mounted near the front of a tip of a handheld part of the 3D scanner system.

FIG. 2 shows an embodiment of this invention where the first light source 210 is mounted near the front of the tip 170.

The advantage of the embodiment in FIG. 1 is that no dichroic mirror is required. On the other hand, it is more challenging to mount the first light source 210 in the typically limited space of the tip or probe 170. Electrical insulation is also more difficult in a location so close to the patient. On the other hand, a side benefit of the arrangement in FIG. 2 is that a metal part of the tip/probe 170 can be used as the heat sink for an LED first light source 210, potentially also heating optical elements in the tip (not shown in FIG. 2) by waste heat. Heating such optical elements can prevent condensation that may otherwise occur when the tip/probe is entered into the patient's oral cavity.

If the first light source 210 emits wavelengths at which the image sensor 180 is responsive, because there is no filtering by any dichroic mirror, it is advantageous to arrange an optical filter 281 in front of the image sensor 180 to block light from the first light source unless the data processing means are configured for distinguishing between light from the first and the second light source. This optical filter allows the wavelengths of the second light source 110 for the 3D surface recording and the emitted fluorescence to pass, but not those exciting the fluorescence. If the light at the first wavelength emitted by the first light source 210 is near or below 400 nm, standard optical elements often act as effective filters, and many image sensors are only poorly sensitive to those wavelengths. In this situation, a dedicated filter 281 may not be needed at all.

Connected to the image sensor 180 is the data processing means 400 comprising a storage medium on which the appropriate algorithms are stored and a CPU configured for executing these algorithms. The data processing means 400 are configured for creating a digital 3D representation of the 3D topography of the teeth based on recorded images comprising probe light reflected from the teeth; for creating a representation of the fluorescence emitted from the fluorescent material of the teeth based on recorded images comprising the emitted fluorescence, and for mapping the representation of the emitted fluorescence onto the corresponding portion of the digital 3D representation of the teeth to provide a combined digital 3D representation.

The 3D scanner system further comprise a visual display unit 500 connected to the data processing means 400 on which visual display unit the combined digital 3D representation is visualized.

The two light sources in the embodiment of FIG. 2 are turned on and off alternatingly in the same manner as described for the embodiment of FIG. 1.

Figure 3:
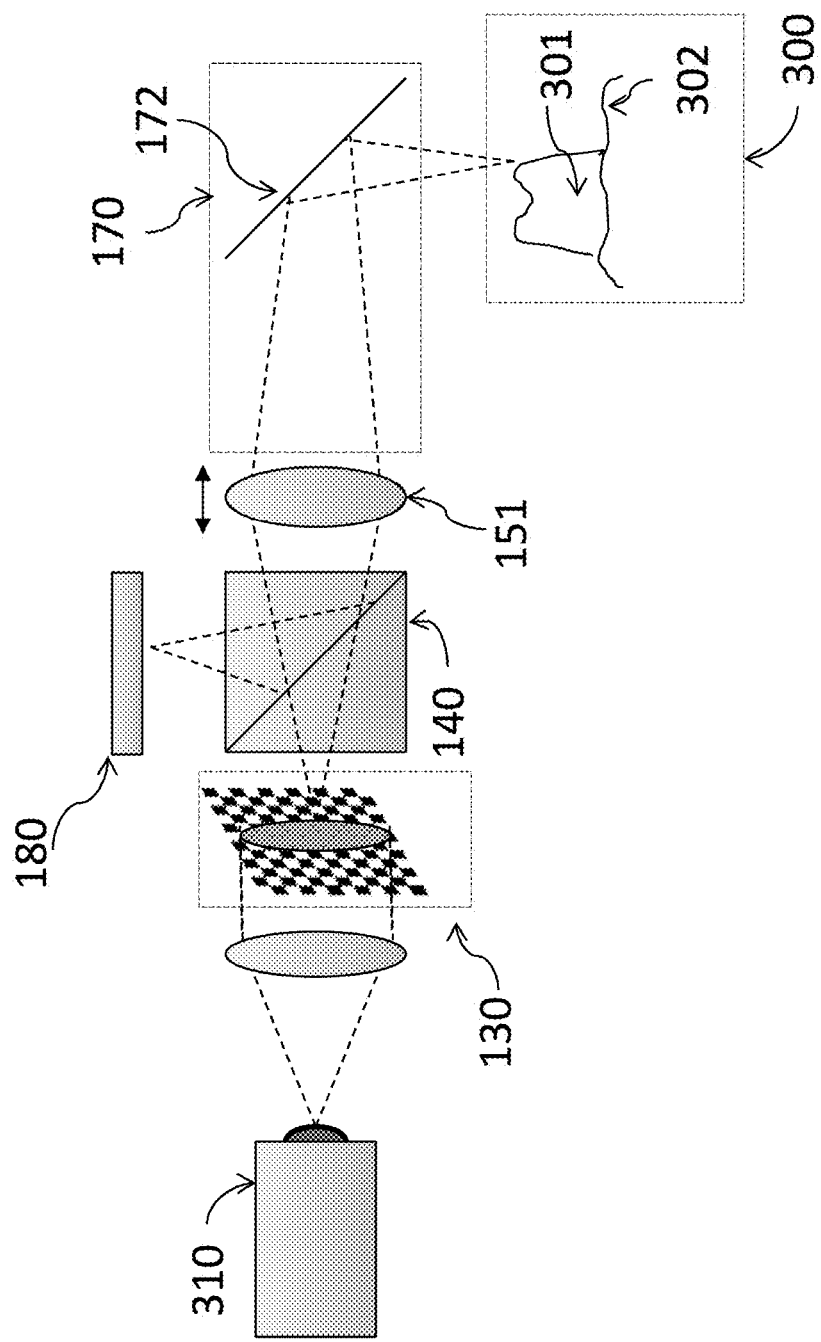
FIG. 3 shows an embodiment of this invention with a single light source.

FIG. 3 shows an embodiment of this invention with a single light source configured for both exciting fluorescence and for recording the 3D surface topography.

The illumination unit is here a single light source unit with only the first light source 310 arranged to illuminate a surface of an intraoral cavity. The first light source 310 emits light with a peak emittance at 405 nm, such that the light from the first light source is suitable for both exciting the fluorescent material in the hard dental tissue 301 and for projecting the pattern 130 onto the region of the intraoral cavity being scanned 300 to record the 3D surface topography of this region. The mirror 172 is reflective both at the wavelength of the light provided by the first light source and at the wavelength of the fluorescence emitted from the hard dental tissue 301, such that light reflected from the surfaces of the intraoral cavity and the fluorescence is collected and guided towards the image sensor 180.

In the illustrated embodiment, the composition of physical elements is as taught in WO2010145669.

The data processing performed by the data processing means may be different. A least partial separation of the signal relating to the fluorescence and the signal relating to the reflected light occurs in the data processing means, as described in the following, and enhanced by appropriate optical design, as described further below.

Figure 4:
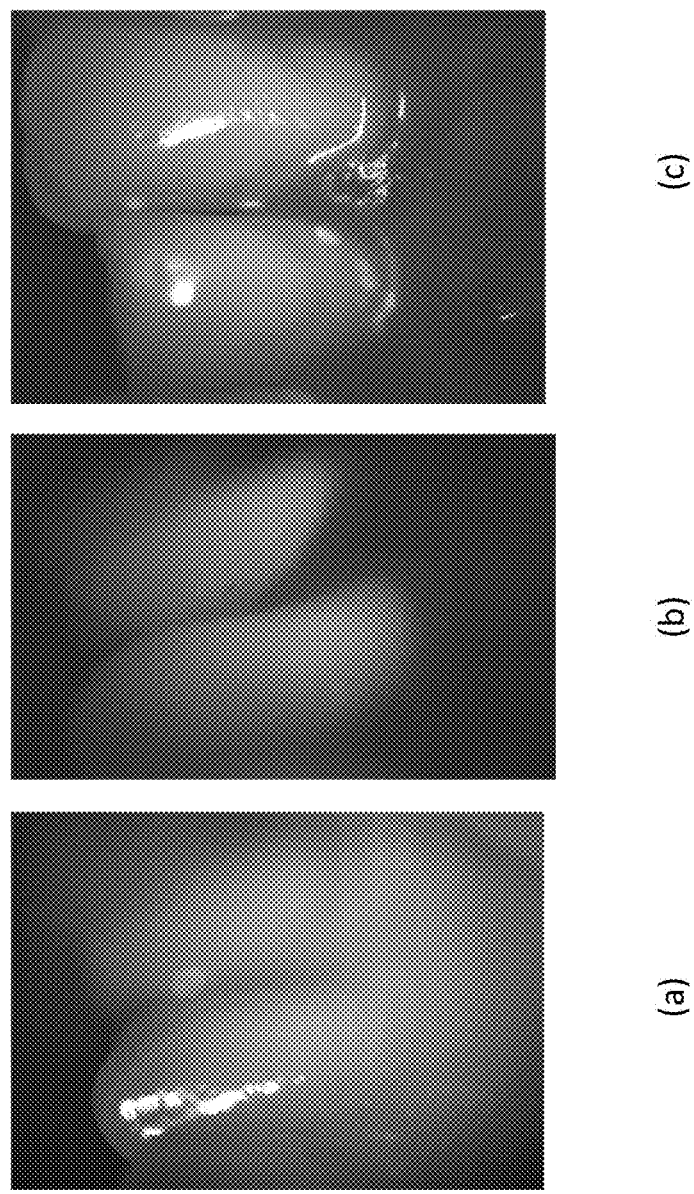
FIG. 4 illustrates how hard and soft dental tissue can be differentiated based on a recorded fluorescence from the hard dental tissue.

FIG. 4 shows the advantage of recording fluorescence for the purpose of differentiating hard and soft dental tissue. The figure shows three images taken by a 3D scanner system according to this invention, taken of similar scenes showing two teeth and at the bottom some gingival in a human intraoral cavity. For image (a), the scene was illuminated with a red LED with peak emission at 630 nm. For image (b), the scene was illuminated with a deep blue LED with peak emission at 400 nm, and a 450 nm long-pass optical filter rejecting radiation at wavelengths below 450 nm was inserted before the image sensor. For image (c), illumination was as in (b), but no optical filter was applied. As can be seen from (a), the difference in reflectance between hard and soft tissue for red light is very small, and hence differentiation is unclear. In image (b) fluorescence from the illuminated region is recorded, and a scan be seen from (b), fluorescence alone yields strong differentiation allowing hard tissue to be distinguished from the soft tissue, but a weaker signal. Note also that as expected when only fluorescence is recorded, no specular reflections are visible in (b), unlike in (a) and (c). Image (c) shows that the combination of reflectance of deep-blue light and the fluorescence emitted from fluorescent materials in the hard dental tissue when excited by the blue light yields a good signal and rather good discrimination. It is not perfect, however, due to some specular reflections from the gingival. Image (c) thus demonstrates that stitching as taught by U.S. Pat. No. 7,698,068 is not optimal. Note that the images are not perfectly sharp because they were taken with the focus lens in one position.

The images in FIG. 4 are also representative of texture images that can be mapped on a digital 3D representation of the 3D surface topography. Note that while 3D coordinates are computed for a block of pixels, the texture represents individual pixels.

WO2010145669 did not differentiate between various contributions to the recorded intensities I, but that additional analysis is fundamental to describe and understand the single light source embodiment of the invention where the soft and hard tissues are distinguished by the data processing means. In particular, I can be written as $$I = I_{sr} + I_{dr} + I_f + I_s \qquad (2)$$

where the subscripts are sr for specular reflection, dr for diffuse reflection including sub-surface reflection, f for fluorescence, and s for stray light. In the following, without loss of generality we assume that $I_s=0$ since the component of stray light is negligibly small or can be compensated for in an appropriate optical design.

When the projection of the pattern 130 is in focus on a part of the intraoral cavity 300 being scanned, the recorded intensity from specular reflection from this in-focus region will display the projected pattern 130 on the image sensor. As a result $I_{sr}$ will vary laterally on the scanned surface. It is advantageous for the 3D scanner to be able to scan the oral cavity with high resolution. Preferably, the lateral resolution is 100 μm or less. This implies the need for the features of the projected pattern to be correspondingly small. The diffusion length of both the light diffusively reflected from the hard tissue and the fluorescence light generated inside the hard tissue is generally longer than 100 μm. Hence $I_{dr}$ and $I_f$ will display little or no lateral variation.

Figure 5A:
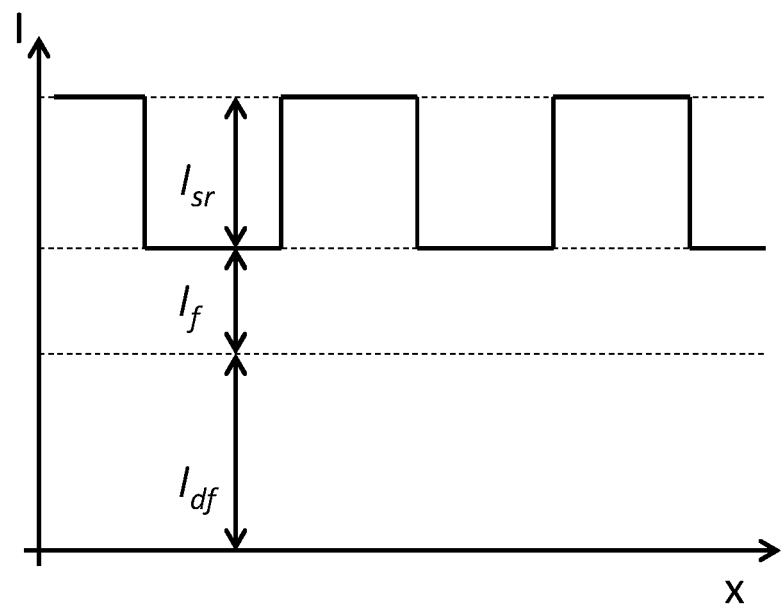
FIGS. 5A and 5B show how the data processing means can analyze the intensity of the light recorded by the image sensor.

FIG. 5A illustrates a part of a recorded image corresponding to an in-focus surface for a single lateral coordinate x, i.e. a coordinate in a plane perpendicular to the line of sight to the surface from the 3D scanner. The relative magnitude of the different components shown in the figure is only for illustrative purposes and may be different in a particular embodiment of the invention. As WO2010145669 teaches, the relevant signal for recording 3D geometry of the intraoral cavity is the intensity due to the specular reflection, $I_{sr}$. WO2010145669 describes ways of using polarizing elements to reduce a signal from the depolarized, diffuse reflection. Light emitted by fluorescence has in similarity to the diffusively reflected light no particular polarization state and will be affected by any polarizing elements in the same manner as diffuse reflection.

The decomposition of intensity expressed in equation (2) can be inserted into equation (1) to describe the decomposition of the correlation measure A. WO2010145669 teaches that it is advantageous that the reference signal f is so normalized that $$\sum_{i=1}^{n} f_i = 0$$

It follows that the contributions to the recorded DC signals from $I_{dr}$ and $I_f$ do not contribute or at least not significantly to the correlation measure A.

Figure 5B:
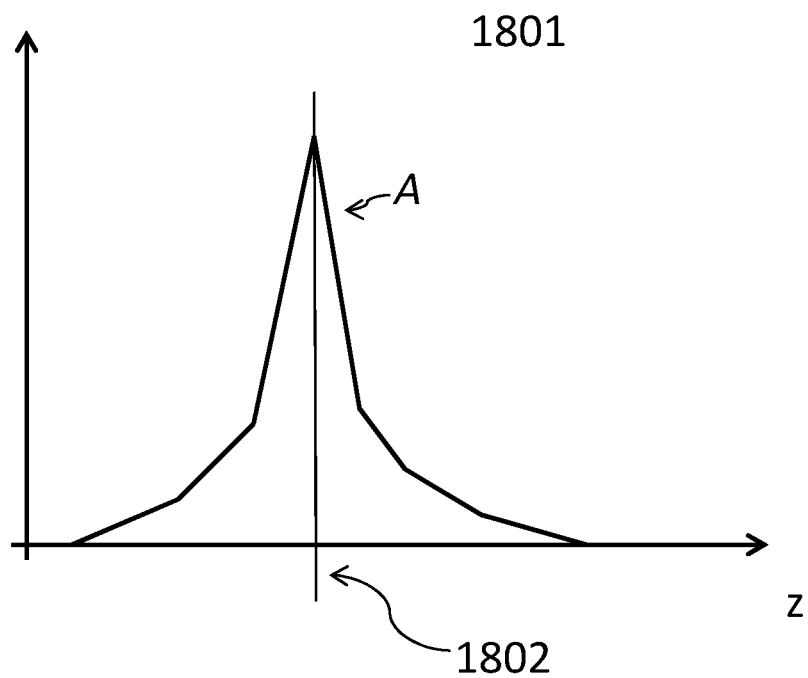

FIG. 5B shows an example for a focus sweep of a given pixel block, i.e., with A as a function of focus lens position z. At location 1802, the projection of the pattern is in focus on the surface, and hence the correlation measure is at a maximum.

The 3D scanner observes A, the sum of all contributions, but does in itself not provide a strong differentiation of hard from soft dental tissue since the specular reflection is not very different between hard and soft tissue surface. The minimum value of the recorded signal I on the sensor within a group of pixels will correspond to the sum of $I_{dr}$ and $I_f$. It is seen in FIG. 4(c) that the sum of $I_{dr}$ and $I_f$ is higher for hard tissue than for soft tissue and this provides a differentiation of hard and soft tissue.

A calibration step can help quantify the sum $I_{dr}+I_f$. For example, the user of the 3D scanner can be guided to first scan a tooth and then an area of the gingival, such that $(I_{dr}+I_f)$ can be computed as the difference in minimum values of I in an in-focus region (see FIG. 5A). It may be further advantageous to repeat the calibration at varying angles of incidence, in case I is found to depend thereon for a particular case. The angle of incidence need not be measured by any additional instrument; the 3D scanner measures the 3D surface in any case and at least a local gradient approximation can be computed.

The above analysis, as illustrated in FIGS. 5A and 5B, shows is the novelty of some embodiments of this invention over WO2010145669. While the latter only teaches how to find the location of the extremum of A, this invention requires an analysis of the background intensity on the sensor with little or no lateral variation over a pixel group. For additional information on finding the in-focus location by analysis of the variation of A, see particularly the section "Spatial Correlation" and FIG. 18 and the accompanying text of WO2010145669.

One way to enhance the differentiation between hard and soft tissue is to choose optical elements that transmits the fluorescence relatively better. Assuming for the sake of simplicity a first light source emitting light with a single wavelength 405 nm and fluorescence emitted at 520 nm, using the wavelength as subscript, and looking only at the intensity recorded in a single pixel, we can write:

$$I_{sr} \propto I_{0.405} t_{405} r t'_{405}$$

$$I_F \propto I_{0.405} t_{405} \eta t'_{520}$$

where $I_0$ is the intensity emitted from the light source, t is the transmissivity of the optical system along the path from light source to the intraoral cavity, r is reflectivity, $\eta$ is emissivity due to fluorescence, and t' is the transmissivity of the optical system along the path from the intraoral cavity to the image sensor. Because $\eta$ is typically considerably smaller than r, it may be advantageous to provide that the design of the optical system is such that $t'_{520}$ is larger than $t'_{405}$, such that the contribution from fluorescence in the overall signal I is significant.

Another way to enhance the differentiation between hard and soft tissue is to use a blue light source, because diffuse reflection from essentially white teeth shows little dependence on wavelength, whereas red gingival reflects blue light more poorly than red light as also can be seen by comparing FIGS. 4(a) and 4(c).

The advantage of the embodiment in FIG. 3 is the relatively small number of physical elements, but the disadvantage is the loss of power of light available to excite fluorescence, as the light emitted by the single light source has to pass through the pattern, i.e., a partly blocked pathway.

All other elements in FIGS. 2 and 3 and the modes of operation enabled by the embodiments illustrated in FIGS. 2 and 3 are as described for FIG. 1.

Note that in all embodiments, it is not a requirement to know the magnitude of fluorescence perfectly well. In the stitching algorithm, we the weights are only used to express some level of certainty in the classification into hard and soft dental tissue, resp. The weights can be raw values as recorded (for example, intensity or $A_f$), but they can also be a function of those, for example some categorization or non-linear function. This invention recognizes that perfect separation of signals into reflection and fluorescence is not possible in practice and hence is robust to this imperfection.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

REFERENCES

Amaechi B T, and Higham S M: Use of Quantitative Light-induced Fluorescence to monitor tooth whitening. In: Lasers in Dentistry VII, Peter Rechmann, Daniel Fried, Thomas Hennig, Editors, Proceedings of SPIE Vol. 4249 (2001), pp. 157-162.

Angmar-Månsson B and ten Bosch J J: Quantitative light-induced fluorescence (QLF): a method for assessment of incipient caries lesions. Dentomaxillofacial Radiology (2001) 30, pp. 298-307.

Callieri M, Cignoni P, Scopigno R. Reconstructing textured meshes from multiple range+rgb maps.VMV 2002, Erlangen, Nov. 20-22, 2002.

Hartles R L and Leaver G: The Fluorescence of Teeth under Ultraviolet Irradiation. Biochemical Journal, vol. 54, no. 4, pp. 632-638.

Kronfeld T, Brunner D, and Brunnett G: Snake-Based Segmentation of Teeth from Virtual Dental Casts. Computer-Aided Design & Applications, 7(2), 2010, 221-233.

Sinyaeva M L, Mamedov A A, Vasilchenko S Y, Volkova A I, and Loschenov V B: Fluorescence Diagnostics in Dentistry. Laser Physics, Vol. 14, No. 8, 2004, pp. 1132-1140.

EMBODIMENTS

1. A 3D scanner system for detecting and/or visualizing cariogenic regions in teeth based on fluorescence emitted from said teeth, said 3D scanner system comprising:
an illumination unit capable of providing probe light for illuminating the teeth, where said probe light comprises light at a first wavelength which is capable of exciting a fluorescent material of the teeth;
an image sensor for recording images of light received from the illuminated teeth, where said image sensor is capable of detecting fluorescence emitted from said fluorescent material when this is excited by light at said first wavelength;
data processing means configured for:
  i. creating a digital 3D representation of the 3D topography of the teeth based on recorded images comprising probe light reflected from the teeth;
  ii. creating a representation of the fluorescence emitted from the fluorescent material of the teeth based on recorded images comprising the emitted fluorescence, and
  iii. mapping the representation of the emitted fluorescence onto the corresponding portion of the digital 3D representation of the teeth to provide a combined digital 3D representation; and
a visual display unit on which the combined digital 3D representation is visualized.

2. The 3D scanner system according to embodiment 1, wherein the image sensor is capable of detecting light at said first wavelength, and wherein the digital 3D representation of the teeth is created based on light at the first wavelength in said images comprising probe light reflected from the teeth.

3. The 3D scanner system according to embodiment 1 or 2, wherein the probe light comprises light at a second wavelength and the image sensor is capable of detecting light at said second wavelength, and where the digital 3D representation of the teeth is created based on light at the second wavelength in said images comprising probe light reflected from the teeth.

4. The 3D scanner system according to any of the previous embodiments, wherein the illumination unit is configured to provide light only at the first wavelength or only at the second wavelength at any time.

5. The 3D scanner system according to any of the previous embodiments, wherein the representation of the fluorescence is a 2D representation and said mapping comprises folding the 2D fluorescence representation onto the digital 3D representation of the teeth.

6. The 3D scanner system according to any embodiments 1 to 4, wherein the representation of the fluorescence is a 3D representation and said mapping comprises registering the 3D fluorescence representation onto the digital 3D representation of the teeth.

7. The 3D scanner system according to any of the previous embodiments wherein the emission spectrum of said illumination unit is predominantly below 500 nm.

8. The 3D scanner system according to any of the previous embodiments, wherein the first wavelength is within the range of 375 nm to 435 nm, such as in the range of 385 nm to 425 nm, such as in the range of 395 nm to 415 nm, such as in the range of 400 nm to 410 nm.

9. The 3D scanner system according to any of embodiments 3 to 8, wherein the second wavelength is within a range of 500 nm to 850 nm.

10. The 3D scanner system according to any of the previous embodiments, wherein the color image sensor comprises a color filter array comprising a number of filters allowing light at said first wavelength to pass and a number of filters allowing the emitted fluorescence to pass, and where the data processing means bases at least part of the creating of the digital 3D representation of the teeth and at least part of the creating the representation of the fluorescence on the same recorded images.

11. The 3D scanner system according to any of the previous embodiments, wherein the representation of the emitted fluorescence is created by analyzing recorded images to identify sections of these images which correspond to fluorescence emitted from the teeth.

12. The 3D scanner system according to any of the previous embodiments, wherein the 3D scanner system comprises a dichroic mirror configured for having a larger reflection coefficient at said second wavelength than at wavelengths corresponding to the first wavelength and the fluorescence, and wherein the dichroic mirror is arranged such that it guides light from the second light source towards the field of view of the scanner system and allows fluorescence received from the field of view to pass towards the image sensor.

13. The 3D scanner system according to any of the previous embodiments, where the field of view for recording the images comprising probe light reflected from the teeth and for recording the images comprising the emitted fluorescence, are substantially identical.

14. The 3D scanner system according to any of the previous embodiments, wherein the illumination unit, the image sensor and at least one unit of the data processing means are integrated parts of a handheld 3D scanner device of the 3D scanner system.

The invention claimed is:

1. A 3D scanner system configured for displaying a digital representation of a cariogenic region of a tooth and a digital 3D representation of the tooth, the 3D scanner system comprising:
 a 3D intraoral scanner device comprising:
  i. one or more image sensor(s);
  ii. a first light source, the first light source configured to emit light at a first wavelength, wherein the 3D intraoral scanner device is configured such that at least one of the one or more image sensor(s) detects light at the first wavelength, thereby configured to record data for a 3D surface topography of the tooth; and
  iii. a second light source, the second light source configured to emit light at a second wavelength, wherein the 3D intraoral scanner device is configured such that at least one of the one or more image sensor(s) detects light at the second wavelength, thereby configured to record data for the cariogenic region of the tooth,
 a data processor configured for:
  i. converting the data for the 3D surface topography of the tooth into the digital 3D representation of the tooth; and
  ii. converting the data for the cariogenic region into the digital representation of the cariogenic region of the tooth,
 a display configured for visualizing both the digital 3D representation of the tooth and the digital representation of the cariogenic region of the tooth,
 wherein both the digital 3D representation of the tooth and the digital representation of the cariogenic region of the tooth are displayed at the same time,
 wherein the one or more image sensor(s) is a single image sensor,
 wherein the second wavelength is within a range of 500 nm to 850 nm,
 wherein the second light source comprises an LED.

2. The 3D scanner system according to claim 1, wherein the digital 3D representation of the tooth is displayed by itself.

3. The 3D scanner system according to claim 1, wherein both the digital 3D representation of the tooth and the digital representation of the cariogenic region of the tooth are displayed as a combined 3D representation.

4. The 3D scanner system according to claim 1, wherein the second wavelength is selected to excite a fluorescent material of the tooth.

5. The 3D scanner system according to claim 1, wherein the 3D intraoral scanner device is configured to shift between the first light source and the second light source repeatedly, thereby configured to illuminate the tooth successively by the light from the first light source and the second light source.

6. The 3D scanner system according to claim 1, wherein the data processor is an integrated part of the 3D intraoral scanner device.

7. The 3D scanner system according to claim 1, wherein the data processor is external to the 3D intraoral scanner device.

8. The 3D scanner system according to claim 1, wherein a first part of the data processor is integrated with the 3D intraoral scanner device and a second part of the data processor is external to the 3D intraoral scanner device.

9. The 3D scanner system according to claim 1, wherein the 3D intraoral scanner device further comprises a mirror configured to reflect wavelengths generated by the first light source and the second light source.

10. The 3D scanner system according to claim 1, wherein the cariogenic region is a region with caries.

11. The 3D scanner system according to claim 1, wherein the cariogenic region is a region with demineralization.

12. The 3D scanner system according to claim 1, wherein the cariogenic region is present in more or less developed stages in the cariogenic region.

13. The 3D scanner system according to claim 1, wherein the cariogenic region is a region with cariogenic bacteria.

14. The 3D scanner system according to claim 1, wherein the first light source is a laser.

15. The 3D scanner system according to claim 1, wherein the first light source is an LED.

* * * * *